(12) United States Patent
Dong et al.

(10) Patent No.: US 7,364,587 B2
(45) Date of Patent: Apr. 29, 2008

(54) HIGH STRETCH, LOW DILATION KNIT PROSTHETIC DEVICE AND METHOD FOR MAKING THE SAME

(75) Inventors: Jerry Q. Dong, Oakland, NJ (US); John Spiridigloizzi, Sharon, MA (US); Ronald Rakos, Neshanic Station, NJ (US); Krzysztof Sowinski, Wallington, NJ (US); William Quinn, Swampscott, MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 583 days.

(21) Appl. No.: 10/938,919

(22) Filed: Sep. 10, 2004

(65) Prior Publication Data
US 2006/0058862 A1 Mar. 16, 2006

(51) Int. Cl.
*A61F 2/06* (2006.01)
(52) U.S. Cl. .......................................... 623/1.5; 66/195
(58) Field of Classification Search ...... 623/1.49–1.53; 66/195
See application file for complete search history.

(56) References Cited

U.S. PATENT DOCUMENTS

| | | | |
|---|---|---|---|
| 3,623,928 A * | 11/1971 | Wincklhofer et al. | 156/175 |
| 4,047,252 A * | 9/1977 | Liebig et al. | 623/1.52 |
| 5,732,572 A * | 3/1998 | Litton | 66/195 |
| 6,408,656 B1 * | 6/2002 | Ory et al. | 66/195 |
| 6,540,773 B2 | 4/2003 | Dong | |
| 6,547,820 B1 * | 4/2003 | Staudenmeier | 623/1.49 |
| 6,554,855 B1 | 4/2003 | Dong | |

(Continued)

FOREIGN PATENT DOCUMENTS

| | | |
|---|---|---|
| WO | WO 94/06373 | 3/1994 |
| WO | WO 2004/060211 | 7/2004 |

OTHER PUBLICATIONS

Ippoliti et al.; Dacron knitted graft dilation assessment with helical CT scanning after aortoiliac surgery; Gornale Italiano Di Chirurgia Vascolare; vol. 7, No. 3; pp. 201-213.

(Continued)

*Primary Examiner*—Suzette Gherbi
(74) *Attorney, Agent, or Firm*—Hoffmann & Baron, LLP

(57) ABSTRACT

A method for providing dilation resistance to an implantable tubular graft includes the steps of (a) providing a graft having opposed open ends and a textile wall extending in a lengthwise direction therebetween defining a graft diameter, wherein the textile wall has radially extending yarns having a radial extent which inter-engage longitudinally extending yarns having a longitudinal extent to define a textile pattern and further wherein the radially extending yarns are obliquely oriented to the lengthwise direction of the graft, thereby defining a first acute angle from the lengthwise direction of the graft; (b) providing an elongate tubular mandrel having a diameter which differs from the graft diameter by a factor of at least 1.5; (c) positioning the graft over the mandrel to radially distend the graft, thereby reorienting the radially extending yarns to reduce the radial extent and to shift the radially extending yarns to a second acute angle from the lengthwise direction of the graft to define an reoriented textile pattern, wherein the second acute angle is greater than the first acute angle; and (d) heat setting the graft at a first temperature to set the inter-engaging yarns in the reoriented textile pattern to provide a graft with improved dilation resistance.

67 Claims, 20 Drawing Sheets

U.S. PATENT DOCUMENTS

| | | |
|---|---|---|
| 6,939,372 B2 * | 9/2005 | Dong .................. 623/1.13 |
| 7,240,522 B2 * | 7/2007 | Kondou et al. ............ 66/195 |
| 2003/0009210 A1 | 1/2003 | Sowinski et al. |
| 2003/0017775 A1 | 1/2003 | Sowinski et al. |
| 2003/0139806 A1 | 7/2003 | Haverkost et al. |
| 2003/0204235 A1 * | 10/2003 | Edens et al. ............. 623/1.5 |
| 2003/0204241 A1 | 10/2003 | Dong |
| 2004/0182511 A1 * | 9/2004 | Rakos et al. ............. 156/287 |
| 2005/0165366 A1 * | 7/2005 | Brustad et al. ............. 604/264 |

OTHER PUBLICATIONS

Robinson et al. ; Graft dilation following abdominal aortic aneurysm resection and grafting ; The Australian and New Zealand Journal of Surgery, vol. No. 69, No. 12; Dec. 1999; pp. 849-851.

* cited by examiner

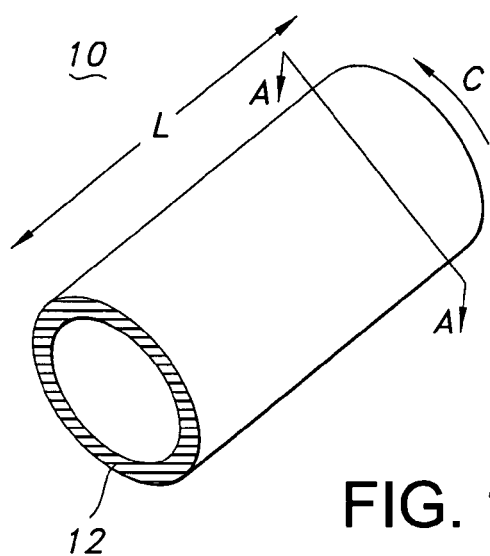
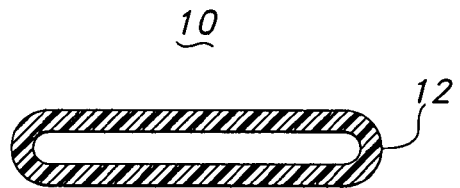
FIG. 3
FIG. 1
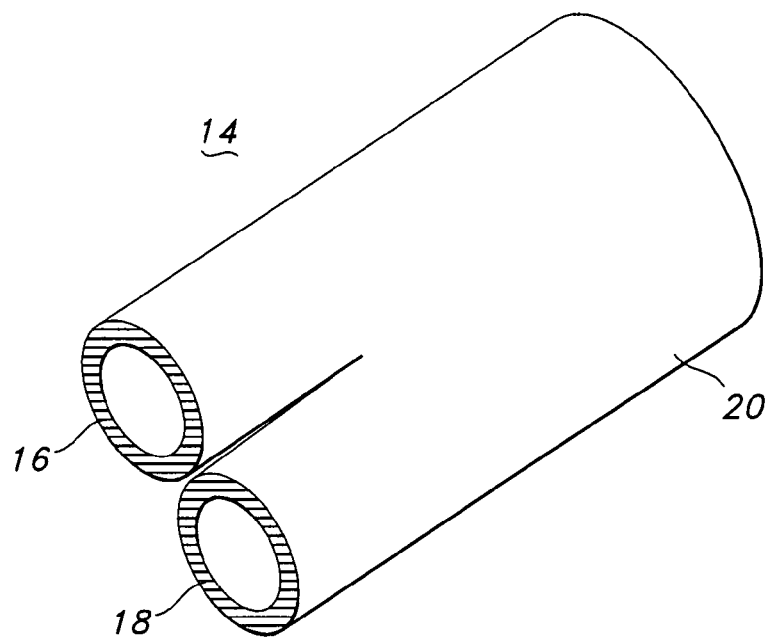
FIG. 2

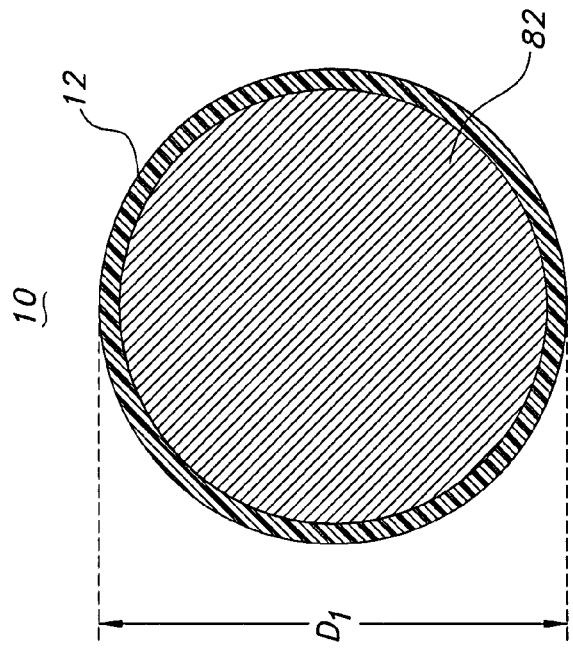
FIG. 10
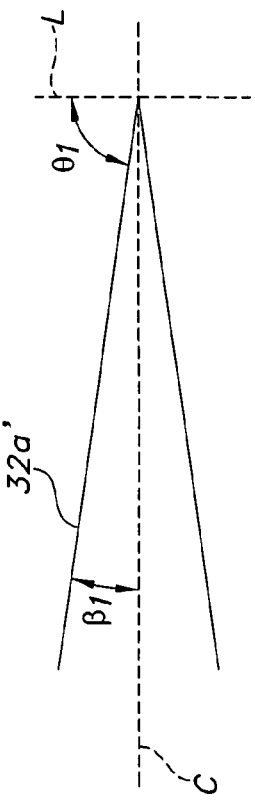
FIG. 13
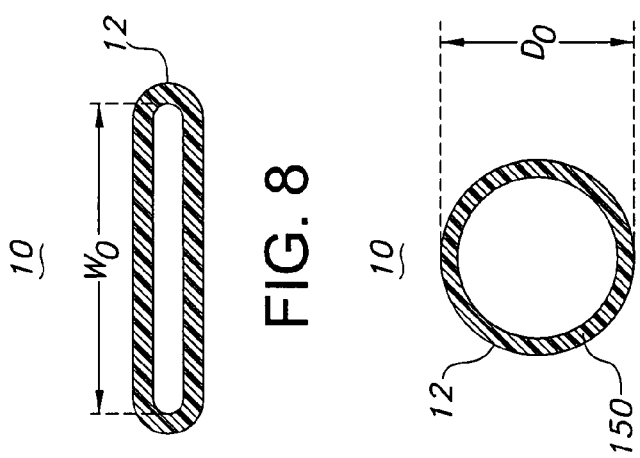
FIG. 8
FIG. 9
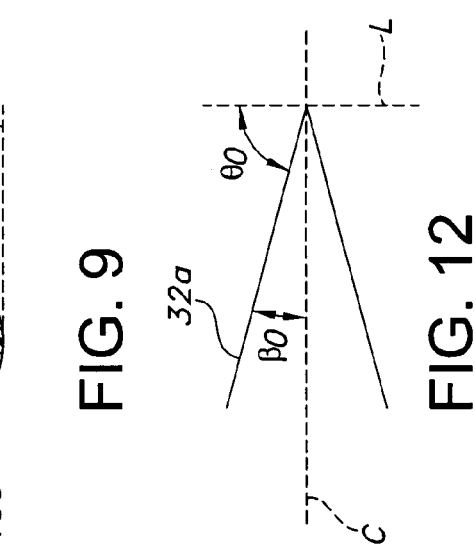
FIG. 12

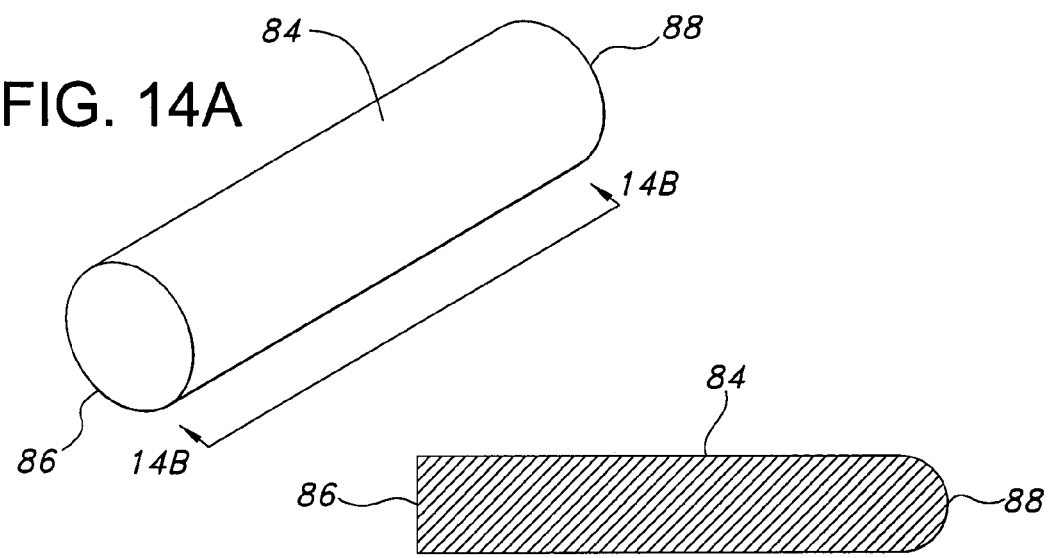
FIG. 14A
FIG. 14B
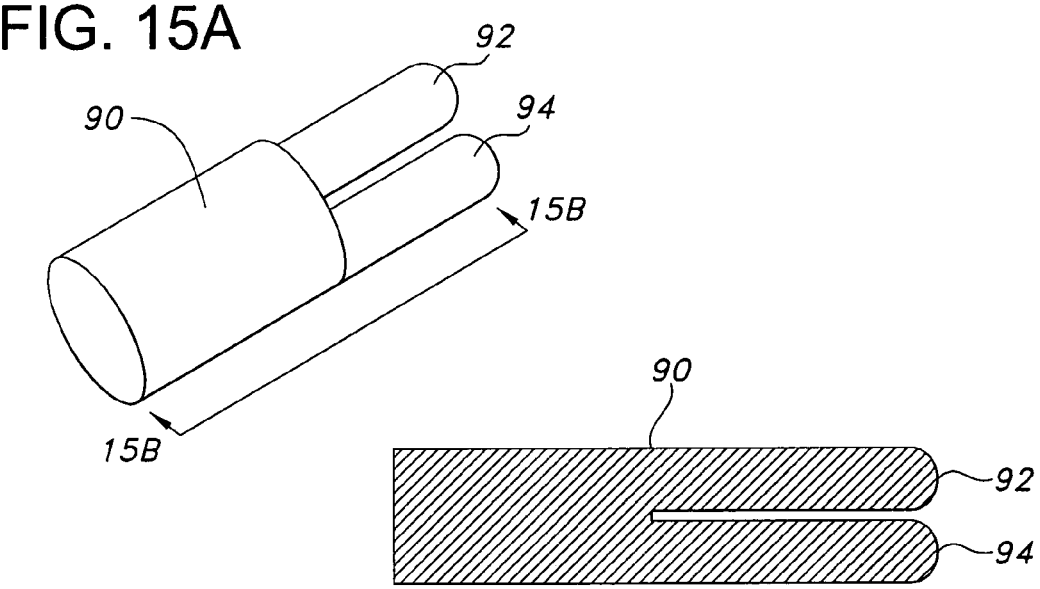
FIG. 15A
FIG. 15B

96

98

100

HIGH STRETCH, LOW DILATION KNIT PROSTHETIC DEVICE AND METHOD FOR MAKING THE SAME

FIELD OF INVENTION

The present invention relates generally to a tubular implantable prosthesis having a textile structure with improved resistance to dilation. More particularly, the present invention relates to an endoprosthesis with a high-stretch, knitted textile structure having reoriented radially extended yarns to increase resistance against dilation, and methods for producing the same.

BACKGROUND OF RELATED TECHNOLOGY

An intraluminal prosthesis is a medical device used in the treatment of diseased blood vessels. An intraluminal prosthesis is typically used to repair, replace, or otherwise correct a diseased or damaged blood vessel. An artery or vein may be diseased in a variety of different ways. The prosthesis may therefore be used to prevent or treat a wide variety of defects such as stenosis of the vessel, thrombosis, occlusion or an aneurysm.

One type of intraluminal prosthesis used in the repair of diseases in various body vessels is a stent. A stent is a generally longitudinal tubular device formed of biocompatible material which is useful to open and support various lumens in the body. For example, stents may be used in the vascular system, urogenital tract, tracheal/bronchial tubes and bile duct, as well as in a variety of other applications in the body. Endovascular stents have become widely used for the treatment of stenosis, strictures and aneurysms in various blood vessels. These devices are implanted within the vessel to open and/or reinforce collapsing or partially occluded sections of the vessel.

Stents generally include an open flexible configuration. This configuration allows the stent to be inserted through curved vessels. Furthermore, this configuration allows the stent to be configured in a radially compressed state for intraluminal catheter implantation. Once properly positioned adjacent the damaged vessel, the stent is radially expanded so as to support and reinforce the vessel. Radial expansion of the stent may be accomplished by inflation of a balloon attached to the catheter or the stent may be of the self-expanding variety which will radially expand once deployed. Structures which have been used as intraluminal vascular grafts have included coiled stainless steel springs; helically wound coil springs manufactured from a heat-sensitive material; and expanding stainless steel stents formed of stainless steel wire in a zig-zag pattern. Examples of various stent configurations are shown in U.S. Pat. No. 4,503,569 to Dotter; U.S. Pat. No. 4,733,665 to Palmaz; U.S. Pat. No. 4,856,561 to Hillstead; U.S. Pat. No. 4,580,568 to Gianturco; U.S. Pat. No. 4,732,152 to Wallsten and U.S. Pat. No. 4,886,062 to Wiktor, all of whose contents are incorporated herein by reference.

A graft is another commonly known type of intraluminal prosthesis which is used to repair and replace various body vessels. A graft provides a lumen through which blood may flow. Moreover, a graft is often configured to have porosity to permit the ingrowth of cells for stabilization of an implanted graft while also being generally impermeable to blood to inhibit substantial leakage of blood therethrough. Grafts are typically tubular devices which may be formed of a variety of materials, including textile and non-textile materials.

A stent and a graft may be combined into a stent-graft endoprosthesis to combine the features thereof. The graft, however, in the stent-graft endoprosthesis should comply with the implantation requirements of the stent which often include collapsing the stent for placement at an implantation site and expansion of the stent for securement thereat. Grafts which cannot easily accommodate the longitudinal and/or radial dimensional changes from an unexpanded or collapsed state to an expanded stent often complicate the implantation of the stent-graft. For instance, some grafts are folded in the collapsed or unexpanded state and must be subsequently unfolded to accommodate the expanded stent. The unfolding of the graft, however, often complicates the placement of the graft on the stent and the implantation of the stent-graft itself. Alternatively, noncontiguous grafts have been used with expandable stent-grafts. Upon expansion of the stent, however, portions of the noncontiguous graft often separate to accommodate the stent expansion. This separation leaves gaps in the graft structure thereby permitting the leakage of blood through these gaps.

Moreover, an intraluminal device, such as a stent, a graft or a stent-graft, may dilate over time after implantation within a bodily lumen. The dilation of the implanted intraluminal device is a radial enlargement of the device resulting from pulsating stresses or pressures present within the bodily lumen. The actions of the pulsating stresses or pressures often fatigue the structure of the device resulting in radial expansion and possibly longitudinal foreshortening.

Thus, there is a need for a graft that compliments the implantation of an expandable stent of a stent-graft endoprosthesis and that limits dilation without the disadvantages of the prior art.

SUMMARY OF THE INVENTION

The present invention is directed to textile grafts that have their radially extending yarns reoriented to provide increased resistance to dilation. The radially extending yards are shifted to a more radially extending orientation than as produced by the knitting or the braiding machine. Such reorientation provides enhanced resistance to dilation while substantially maintaining the desirable features of the textile graft, such as longitudinal stretchablity.

In one aspect of the present invention, a method for providing dilation resistance to an implantable tubular graft is provided. The method includes the steps of (a) providing a graft having opposed open ends and a textile wall extending in a lengthwise direction therebetween defining a graft diameter, wherein the textile wall has radially extending yarns having a radial extent which inter-engage longitudinally extending yarns having a longitudinal extent to define a textile pattern and further wherein the radially extending yarns are obliquely oriented to the lengthwise direction of the graft, thereby defining a first acute angle from the lengthwise direction of the graft; (b) providing an elongate tubular mandrel having a diameter which differs from the graft diameter by a factor of at least 1.5; (c) positioning the graft over the mandrel to radially distend the graft, thereby reorienting the radially extending yarns to reduce the radial extent and to shift the radially extending yarns to a second acute angle from the lengthwise direction of the graft to define a reoriented textile pattern, wherein the second acute angle is greater than the first acute angle; and (d) heat setting the graft at a first temperature to set the inter-engaging yarns in the reoriented textile pattern to provide a graft with improved dilation resistance.

Desirably, the mandrel has a diameter from about 1.5 to about 3.0 times greater than the diameter of the graft. Further, the mandrel may be a non-elastomeric material or a metallic material, for example, a stainless steel material.

The radially extending yarns and the longitudinally extending yarns may be inelastic yarns, for example, fully drawn, non-texturized polyethylene terephthalate yarns. Further, the textile pattern may be a knitted textile pattern, such as a high stretch knit pattern having a one needle overlap and a two needle or greater underlap, or a braided textile pattern. When the textile pattern is a knitted pattern, the step of positioning the graft over the mandrel further includes radially distending the graft without substantially changing the length of the graft.

The step of providing a mandrel may further include the step of providing at least two mandrels of different diameters, and wherein the step of positioning the graft includes positioning the graft over a first mandrel and then positioning the graft over the second mandrel, wherein the diameter of the second mandrel is larger than the diameter of the first mandrel.

Further, the mandrel desirably has a rounded end and the graft is passed over the rounded end of the mandrel.

Still further, the mandrel may be tapered to provide a first end with a first diameter and a second end with a second diameter, wherein the second diameter is larger that the first diameter and further wherein the second diameter is at least a multiplicative factor of 1.5 times greater than the graft diameter. The step of positioning the graft further includes positioning the graft over the first end of the mandrel and sliding the graft towards the second end of the mandrel. Desirably, the first end of the mandrel is a rounded end.

Mandrels having a smooth exterior surface with a roughness less than about 8 microinches or less than about 0.2 micrometers are useful with the methods of the present invention. Such roughness values are grade 4 or finer as defined by industry standards.

The method of the present invention may suitably be used to improve dilation resistance to a bifurcated graft. In such a case, a bifurcated mandrel is typically used.

The methods of the present invention may further include the step of: (i) removing the graft from the mandrel after the heat-setting of the graft; (ii) positioning the graft over a second mandrel which has a smaller diameter than the elongate tubular mandrel; and (iii) heat setting the graft over the second mandrel at a second heat-setting temperature which is greater than the first heat-setting temperature. Desirably, a tubular layer or sheet of expanded polytetrafluoroethylene over the second mandrel prior to the step of positioning the graft on the second mandrel. The second heat-setting temperature, which is typically greater than the first heat setting temperature, bonds portions of the expanded polytetrafluoroethylene to portions of the graft. When the graft is a bifurcated graft having a main tubular graft body and at least two tubular graft legs extending from one end of the main tubular graft body; the mandrel is desirably a bifurcated mandrel having a main tubular mandrel body portion and at least two tubular mandrel leg portions extending from one end of the main tubular mandrel body; and the expanded polytetrafluoroethylene is positioned over at least one of the mandrel portions.

Grafts made by the methods of the present invention have less than about 15 percent radial elongation under a force of about two pounds-force, which represents a considerable improvement over the prior art. The two-pound force (or about 100 mm Hg) represents a higher pressure than is normally experienced in the human vascular system. For example, the mean aortic pressure is about 95 mm Hg in a normal individual. Grafts made by the methods of the present invention are also thin-walled, i.e., less than about 0.4 millimeters in wall thickness, and do not substantially expand in diameter when subjected to normal physiological pressures within body lumens, i.e., resistant against dilation.

In another aspect of the present invention, a method for providing dilation resistance to an implantable knitted tubular graft includes the steps of (a) providing a graft having opposed open ends and a textile wall extending in a lengthwise direction therebetween defining a graft diameter, wherein the textile wall has course yarns having a radial extent which inter-loop wale yarns having a longitudinal extent to define a knitted textile pattern and further wherein the course yarns are obliquely oriented to the lengthwise direction of the graft, thereby defining a first acute angle from the lengthwise direction of the graft; (b) providing an elongate tubular mandrel having a diameter which is greater than the graft diameter by a factor of at least 1.5; (c) positioning the graft over the mandrel to radially distend the graft, thereby reorienting the course yarns to reduce the radial extent and to shift the course yarns to a second acute angle from the lengthwise direction of the graft to define a reoriented textile pattern, wherein the second acute angle is greater than the first acute angle; and (d) heat setting the graft at a first temperature to set the inter-looping yarns in the reoriented textile pattern to provide a graft with improved dilation resistance. Desirably, the knitted pattern is a warp knitted pattern. More desirably, the knitted textile pattern is a high stretch knit pattern having a one needle overlap and a two needle or greater underlap. Further, the step of positioning the graft over the mandrel further includes radially distending the graft without a substantially changing length of the graft. Still further, the graft may be a bifurcated graft.

The method of this aspect of the present invention may further include the steps of: (i) removing the graft from the mandrel after the heat-setting of the graft; (ii) positioning a tubular layer or sheet of expanded polytetrafluoroethylene over a second mandrel which has a smaller diameter than the elongate tubular mandrel; (iii) positioning the graft over the second mandrel; and (iv) heat setting the tubular layer or sheet of expanded polytetrafluoroethylene and the graft over the second mandrel at a second heat-setting temperature which is greater than the first heat-setting temperature. The second heat-setting temperature bonds portions of the expanded polytetrafluoroethylene to portions of the graft.

The graft made by the method of this aspect of the present invention desirably has less than about 15 percent radial elongation under a force of about two pounds-force. Further, the graft made by the method of this aspect of the present invention may have are also thin-walled, i.e., less than about 0.4 millimeters in wall thickness, and do not substantially expand in diameter when subjected to normal physiological pressures within body lumens, i.e., resistant against dilation.

BRIEF DESCRIPTION OF THE DRAWINGS

FIG. 1 is a perspective view of a single lumen endoprosthesis of the present invention.

FIG. 2 is a perspective view of a bifurcated endoprosthesis of the present invention.

FIG. 3 is a cross-sectional view of the endoprosthesis of FIG. 1 depicted as a flat-knitted tubular structure.

FIG. 8 is a cross-sectional view of a graft of the present invention having a flat-knitted width of $W_0$.

FIG. 9 is a cross-sectional view of the graft of the FIG. 8 having a circular diameter of $D_0$.

FIG. 10 is a cross-sectional view of the graft of the FIG. 9 disposed over a mandrel having a circular diameter of $D_1$.

FIG. 11 is a depiction of the graft of FIG. 8 after it has been placed over a large diameter mandrel.

FIG. 12 is an illustration of a radially extending yarn of the graft of FIG. 8.

FIG. 13 is an illustration of a reoriented radially extending yarn of the graft of FIG. 11.

FIGS. 14A and 14B depict a mandrel useful with the present invention.

FIGS. 15A and 15B depict a bifurcated mandrel useful with the present invention.

DETAILED DESCRIPTION OF THE INVENTION

Figure 4A:
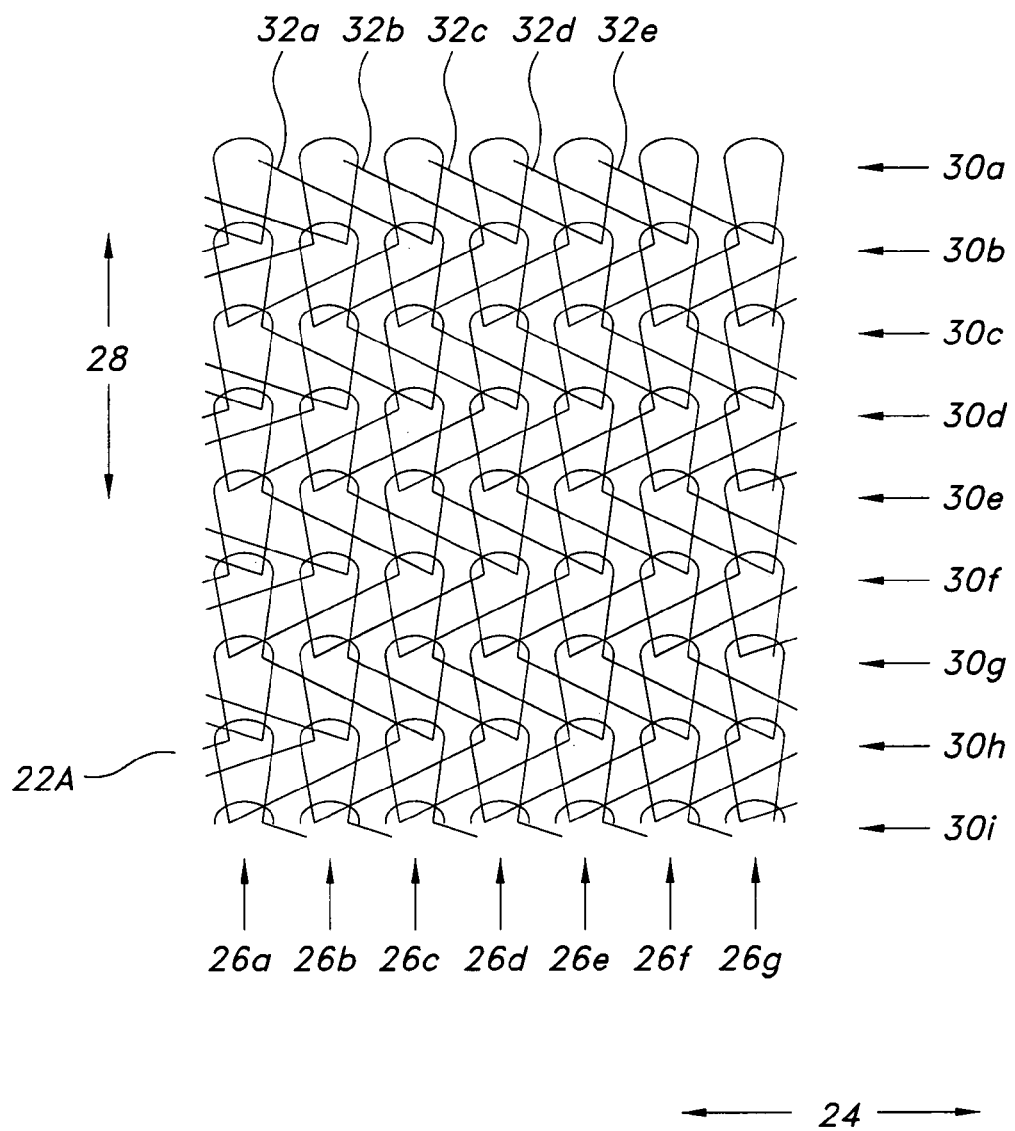
FIG. 4A is an illustration of a textile portion having a two-needle underlap of the graft of FIG. 1 taken along a surface portion of the graft indicated by the A-A axis.

The present invention is an implantable medical device having a reoriented textile pattern to provide for improved resistance to dilation. Desirably, the textile pattern is a knitted or a braided textile pattern to also provide for longitudinal flexibility or stretchability. Such textile patterns typically have radially extending yarns that are not parallel to the radial or circumferential axis of the device. The radial extending yarns are reoriented by the methods of the present invention to a second or different position that is more parallel to the radial or circumferential axis. The shifting of these radially extending yarns provides for improved resistance to dilation while not substantially limiting longitudinal stretchability, as contrasted to woven grafts which have radially extending yarns that are parallel to the circumferential axis but have only very limited longitudinal stretchability.

The textile medical device of the present invention may be a hollow tubular prosthesis 10, as illustrated in FIG. 1. The prosthesis 10 is a single lumen device defined by a cylindrical wall 12. The present invention, however, is not limited to composite textile constructions of single lumen construction. For example, a multi-lumen prosthesis, such as bifurcated prosthesis 14, may suitably be provided with a composite textile construction. As depicted in FIG. 2, bifurcated prosthesis 14 includes two hollow tubular legs 16, 18 and a main hollow tubular body 20.

In one aspect of the present invention, the prostheses 10 and 14 are knitted textile grafts. Knitting involves the interlooping or stitching of yarn into vertical columns (wales) and horizontal rows (courses) of loops to form the knitted fabric structure. Warp knitting is particularly useful with the textile prostheses 10 and 14 of the present invention. In warp knitting, the loops are formed along the textile length, i.e., in the wale or warp direction of the textile. For a tubular textile, such as textile prostheses 10 and 14, stitches in the axial or longitudinal direction of the tubular textile are called wales and stitches in the radial or circumferential direction of the tubular textile are called courses.

Conventional knitted tubular grafts often had to reduce the number of wales per inch to reduce the tendency of a graft to dilate. A low number of wales per inch, however, often reduce compliance of the graft where the graft may not be fluid-tight, i.e., preventing flow of blood therethrough, without other sealing mechanisms. Conventional grafts also used inelastic or a combination of inelastic and elastic yarns to limit radial expansion of a knitted textile graft. The textile prostheses 10 and 14 of the present invention are not so limited. The textile prostheses 10 and 14 use a reoriented knit pattern which by itself substantially inhibits undesirable radial expansion. Moreover, the reoriented knit pattern of the present invention allows for radial contraction and longitudinal elongation of the textile prostheses 10 and 14 while still providing a constraint to limit radial expansion.

Moreover, conventional knitted tubular grafts often had to reduce or limit the number of courses per inch to obtain a flexible tubular structure, i.e., a structure with longitudinal stretchability. Reducing the number of courses per inch, however, opens the macroporous structure of the textile. A macroporous textile structure is not desirable as a graft because such a structure is not a fluid tight structure, i.e., blood will flow through the graft. Similarly, if the number of wales per inch was too low, the graft would not seal blood flow. If the number of wales per inch was too high, the graft could dilate with time. Thus, conventional grafts were limited by the total number of courses and wales per inch, which is referred to as the number of picks per square inch or the pick size.

For example, U.S. Pat. No. 5,732,572 to Litton describes a textile tubular prosthesis in a warp-knit having an underlap of greater than two needle spaces to limit dilation. The prosthesis, however, is limited to a pick size of 80 to 350 stitches per square centimeter (520 to 2,260 stitches per square inch) to provide a longitudinally stretchable tubular structure. Such a pick size represents about 9 to 19 courses or wales per centimeter (23 to 48 courses or wales per inch). With such a low pick size the prosthesis of the prior art is knitted in multiple layers to provide a fluid tight structure while maintaining some degree of stretchability and resistance to dilation. The textile prostheses 10 and 14 of the present invention is not so limited because of the novel knit pattern used to form the graft as compared to more conventional knit patterns, such as tricot, locknit and the like, or even other stretchable knit patterns interlaced with these patterns.

Moreover, grafts are sometimes crimped with creases or folds which tend to reduce kinking when the graft is bent. The kinking also allows for some elongation of the graft, but such a crimped graft is sometimes not useful as a stent-graft because of the gaps that would result between the stent and the crimped graft.

The textile prostheses 10 and 14 are configured to have a high degree of stretchability. As used herein, the term stretchability and its variants refer to a textile capable of substantially reversible elongation between a quiescent state and a stretched state. Desirably, the stretchability of the textile prostheses 10 and 14 are substantially compatible with the dimensional changes associated with an expandable stent having both an expanded and an unexpanded or a contracted state as discussed above. Moreover, textile prostheses 10 and 14 do non-bulgingly contract from the elongated state to the quiescent state. The textile prostheses 10 and 14 substantially abut an associated stent or stents along both circumferential and longitudinal portions of the stent without separating or bulging from the stent.

Knitting patterns useful in providing desirable limits to radial expansion while maintaining the desired longitudinal stretchability include those knitting patterns that are not highly interlaced, such as certain conventional patterns that interlace each adjacent back and front yarns. An example of a highly interlaced and commonly known knitted pattern is a Tricot or Jersey pattern. In contrast the knitting pattern of the present invention is not highly interlaced to provide, among other things, the stretchability of the textile graft for use with an expandable stent.

Further, prostheses 10 and 14 are typically flat knitted. As depicted in FIG. 3, which is a cross-sectional view of a flat knitted prosthesis as produced on a knitting machine (not shown), prosthesis 10 is kitted as a substantially flat, but continuous tubular wall. In other words, the prostheses 10 and 14 are continuous textile tubular structures that are not formed from suturing or otherwise securing planar sheets of textile fabric.

FIG. 4A is an illustration of portion 22A of textile prosthesis 10 taken along the A-A axis. The knitted portion 22A is characterized as a two needle underlap with a one needle overlap. In FIG. 4A, needle positions in the course direction, i.e., vector 24, are noted by element numbers 26a through 26g and needle positions in the wale direction, i.e., vector 28, are noted by element numbers 30a through 30i. Yarn 32a travels in the course direction from needle position 26a to needle position 26c, or two needle positions, before interlooping with yarn 32c. Yarn 32a then travels two needle positions in the opposite course direction to interloop with a yarn. This alternating two needle position movement is repeated with different yarns to form a knitted pattern with a two needle underlap.

The two needle underlap knitted portion 22A is depicted as a single knitted layer in FIG. 4A, however, the textile prosthesis 10 of the present invention is not so limited. For instance, the knitted portion 22A may include more than one layer of interconnected yarns. In such a multi-layered knitted textile, yarns from one layer are often interlooped with yarns in another layer to form the multi-layered knitted textile.

As described above, textile prosthesis 10 is a flat-knitted tubular structure. To form such a flat-knitted tubular structure, two portions 22A are co-knitted and connected to one and the other joined together by border yarns.

Figure 5A:
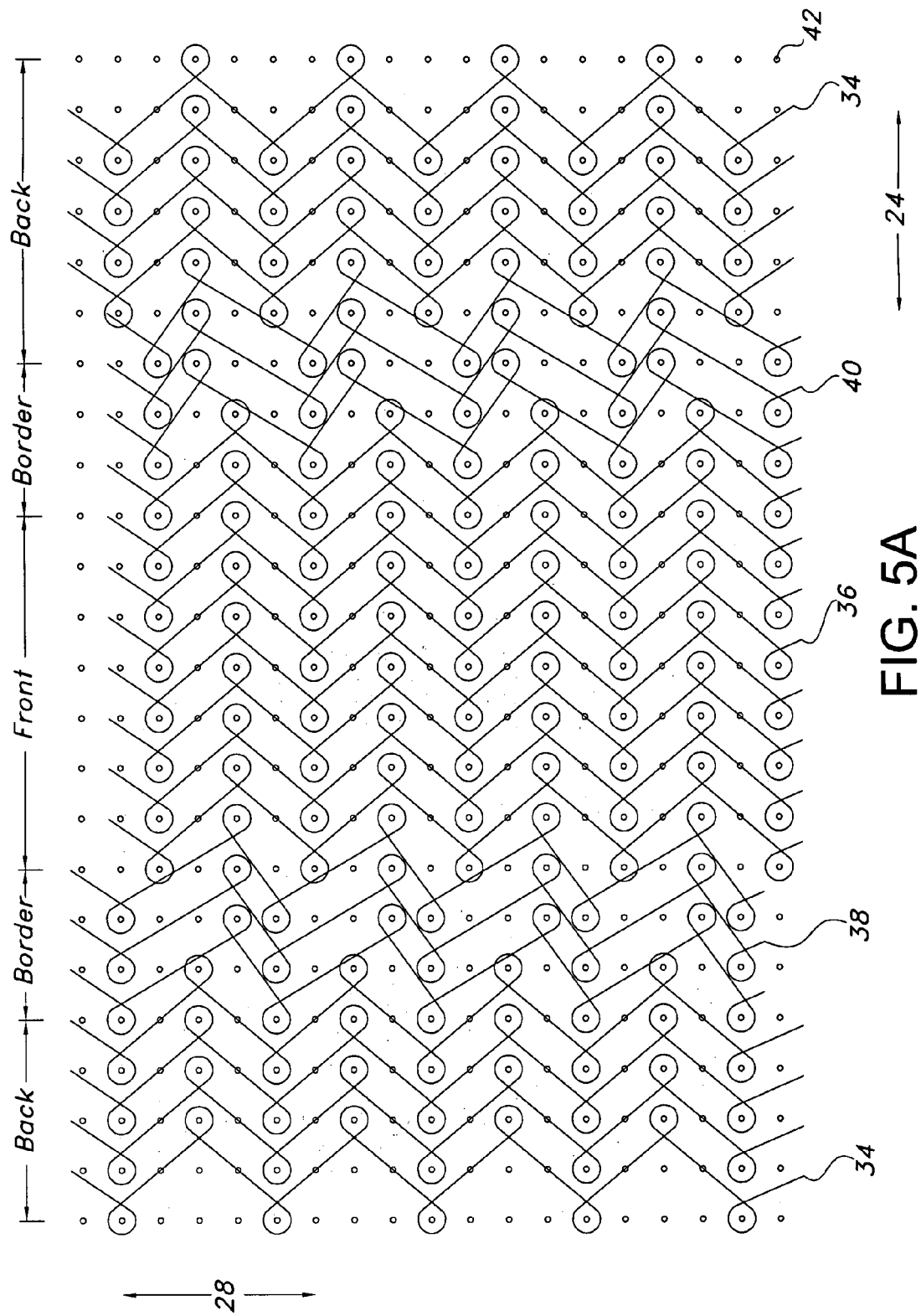
FIGS. 5A and 6A depict two-needle underlap yarn patterns for the textile portion of FIG. 4A.

FIG. 5A depicts the two needle underlap yarn patterns of FIG. 4A by separating the front, back and border yarns from one and the other to more clearly illustrate the individual yarn knit pattern and the repeating nature, if any, of these individual yarn knit patterns. As depicted in FIG. 4A, front yarn 36 and back yarn 34 are repeated about 8 times. Border yarns 38 and 40 alternately repeat about three times between the repeating front and back yarn patterns. The front yarn pattern is repeated to yield the technical front or the exterior surface of the textile prosthesis 10 of the present invention. The back yarn pattern is repeated to yield the technical back or the interior surface of the textile prosthesis 10 of the present invention.

Figure 6A:
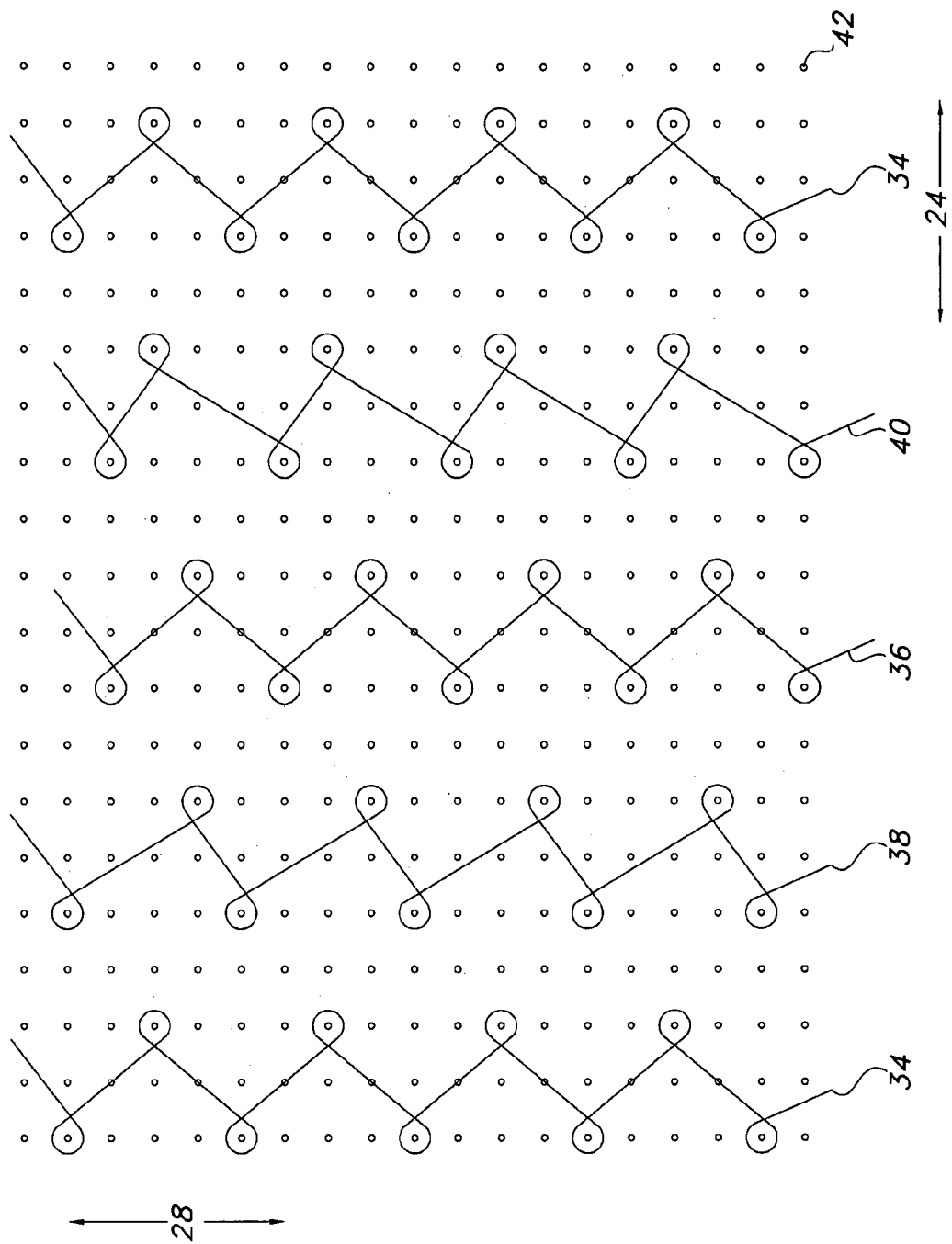

The two needle underlap knitting patterns for the front and back yarns are further illustrated in FIG. 6A. The front, back and border yarns are interlaced in a relatively loose pattern having an underlap of at least two needle positions, which are depicted as dots 42. As used herein the term underlap and its variants refer to a yarn that traverses one or more yarns before forming an interlacing loop with a yarn. Such a pattern not only provides stretchability to the textile prosthesis 10 but also provides resistance against dilation. Not wishing to be bound by any particular theory, it is believed that the long underlap in the course direction, which is indicated as vector 24, reduces the potential for expansion in the wale direction, which is indicated by vector 28, because the underlap in the course direction inhibits undesirable radial expansion.

As shown in FIG. 6A, back yarns 34 and front yarns 36 shift diagonally by at least two needle positions in alternating closed-loop interlacing structures. As used herein, closed-loops refer to interlacing yarns where a front or a back yarn crosses over itself in forming the loop. Other patterns useful with the practice of the present invention, such as border patterns, are illustrated in FIG. 6A.

Figure 4B:
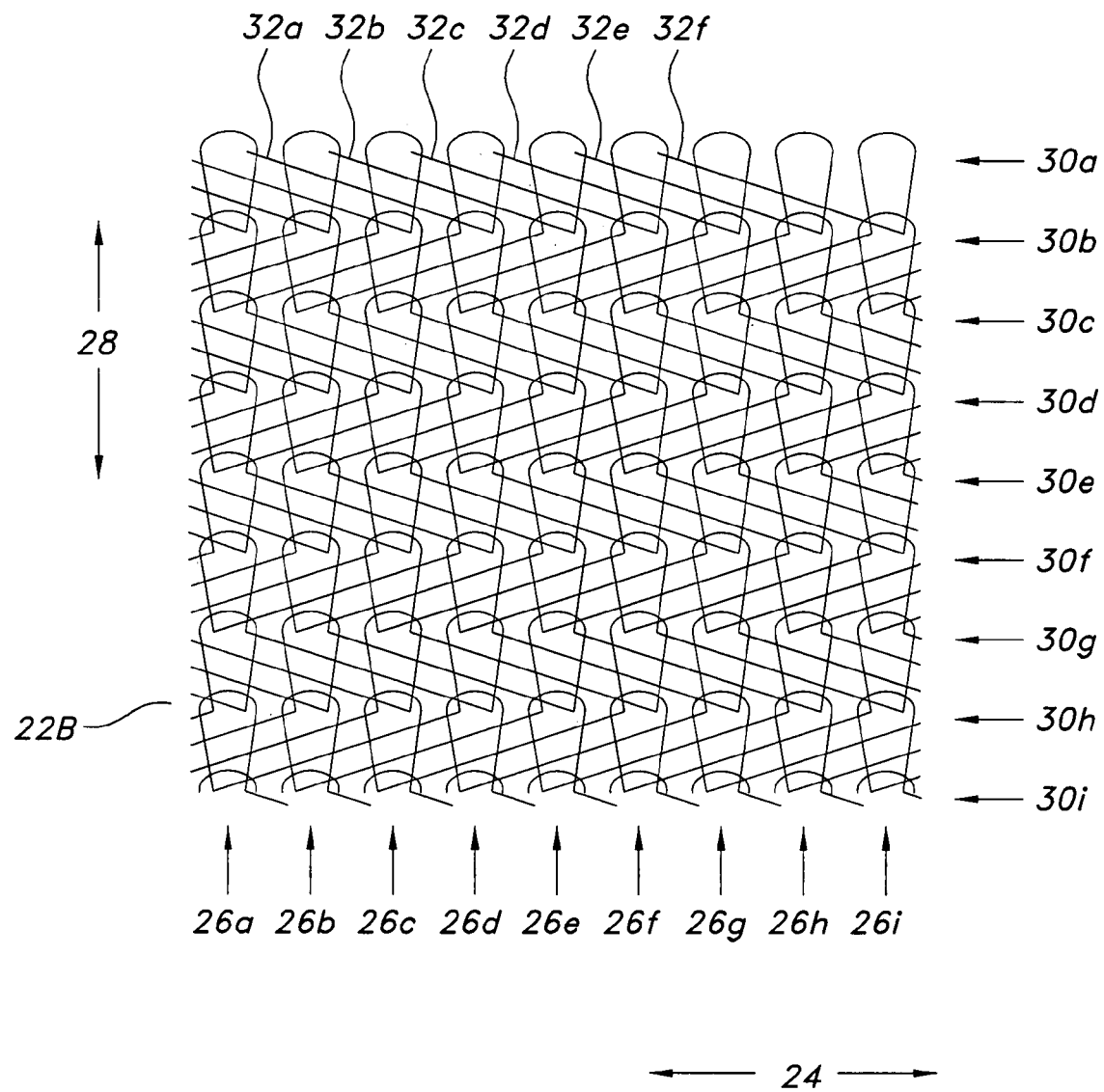
FIG. 4B is an illustration of a textile portion having a three-needle underlap of the graft of FIG. 1 taken along a surface portion of the graft indicated by the A-A axis.

FIG. 4B is an illustration of portion 30B of textile prosthesis 10 taken along the A-A axis. The knitted portion 30B is characterized as a three-needle underlap with a one needle overlap. In FIG. 4B, needle positions in the course direction, i.e., vector 24, are noted by element numbers 26a through 26i and needle positions in the wale direction, i.e., vector 28, are noted by element numbers 30a through 30i. Yarn 32a travels in the course direction from needle position 26a to needle position 26d, or three needle positions, before interlooping with yard 32d. Yarn 32a then travels three needle positions in the opposite course direction to interloop with a yarn. This alternating three needle position movement is repeated with different yarns to form a knitted pattern with a three needle underlap.

The knitted portion 30B is depicted as a single knitted layer in FIG. 4B, however, the textile prosthesis 10 of the present invention is not so limited. For instance, the knitted portion 30B may also include more than one layer of interconnected yarns. In such a multi-layered knitted textile, yarns from one layer are often interlooped with yarns in another layer to form the multi-layered knitted textile.

Figure 5B:
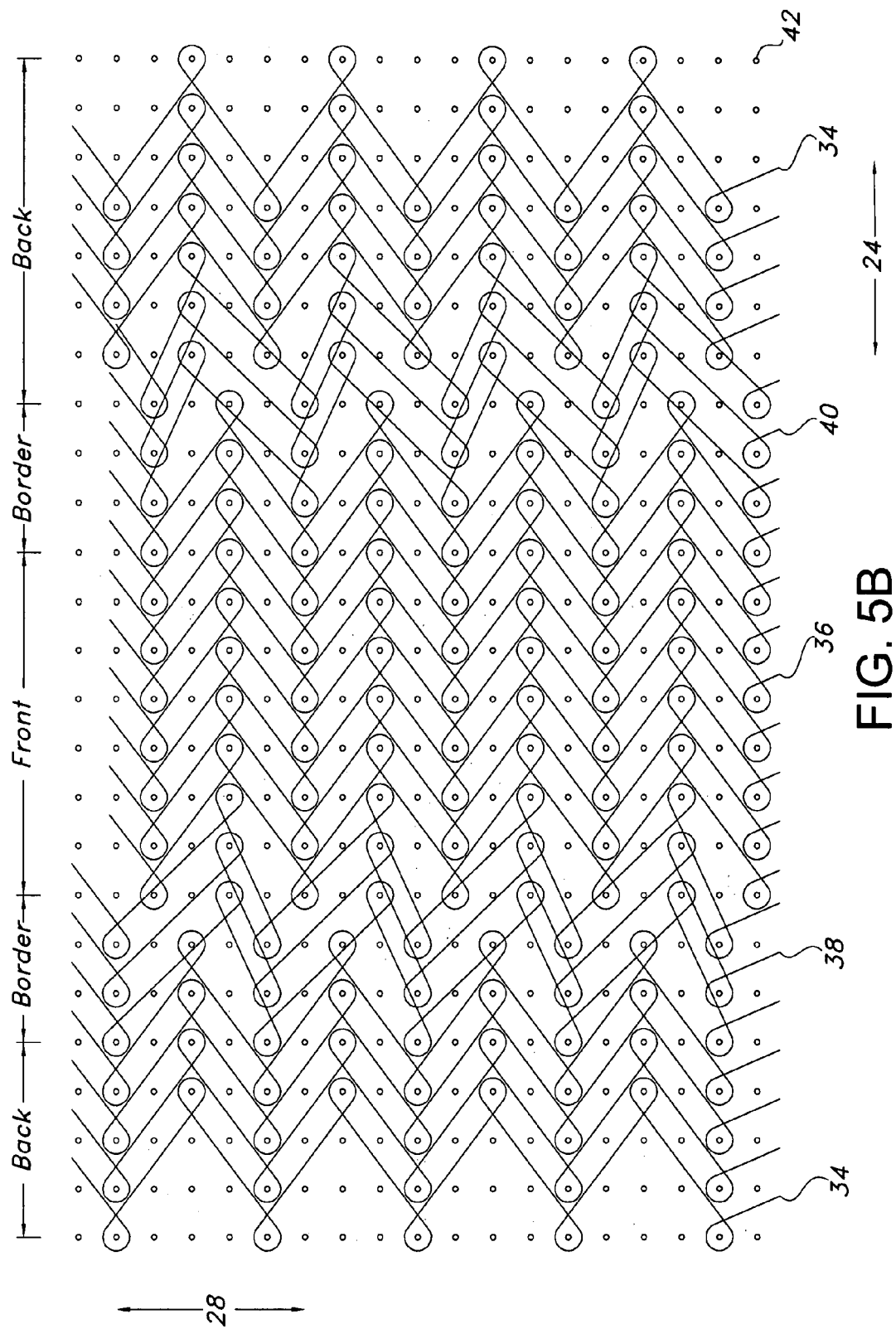
FIGS. 5B and 6B depict three-needle underlap yarn patterns for the textile portion of FIG. 4B.

FIG. 5B depicts the three-needle underlap yarn patterns of FIG. 4B by separating the front, back and border yarns from one and the other to more clearly illustrate the individual yarn knit pattern and the repeating nature, if any, of these individual yarn knit patterns. As depicted in FIG. 4B, front yarn 36 and back yarn 34 are repeated about 8 times. Border yarns 38 and 40 alternately repeat about three times between the repeating front and back yarn patterns. The front yarn pattern is repeated to yield the technical front or the exterior surface of the textile prosthesis 10 of the present invention. The back yarn pattern is repeated to yield the technical back or the interior surface of the textile prosthesis 10 of the present invention.

Figure 6B:
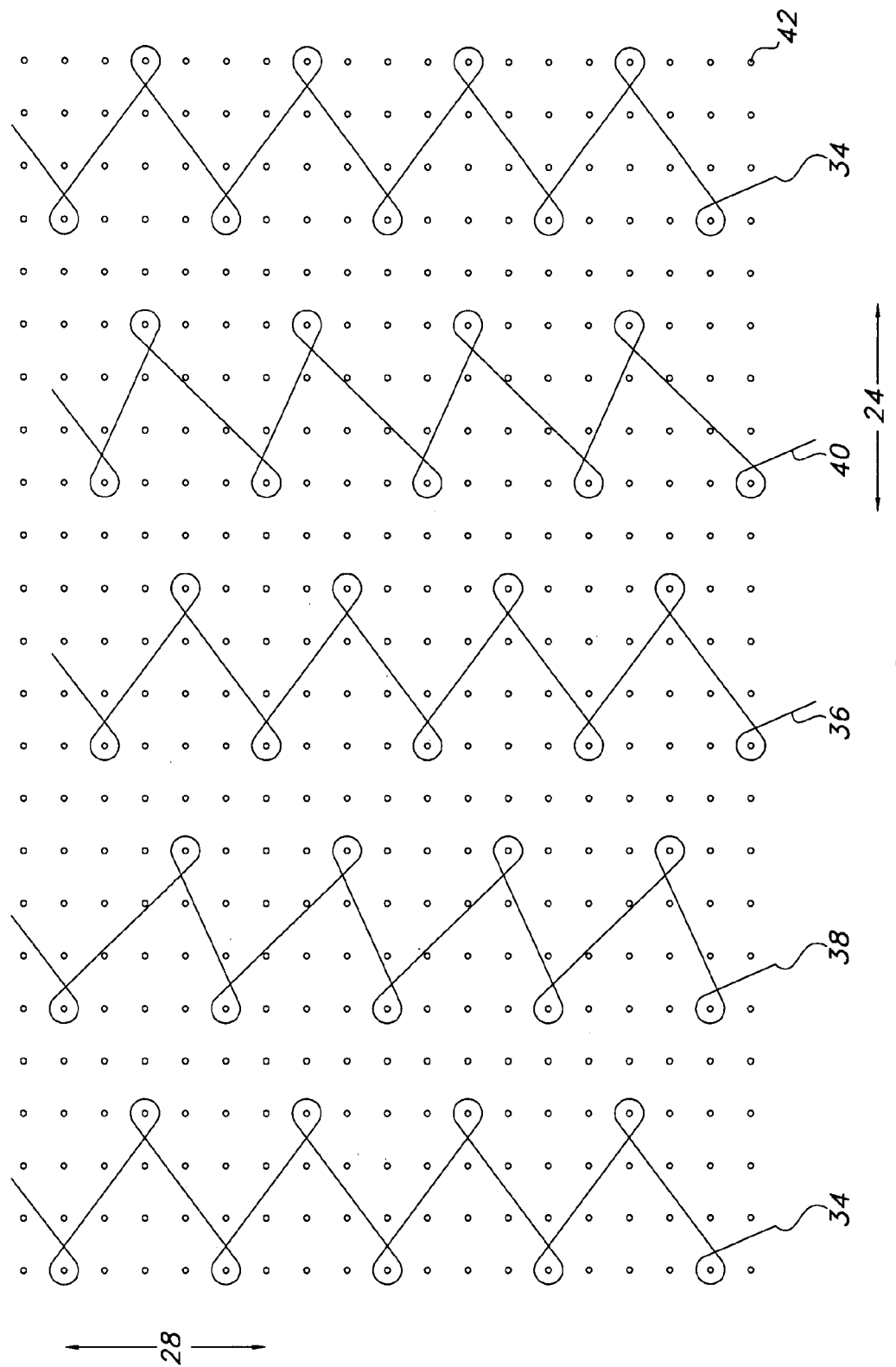

The three-needle underlap knitting patterns for the front and back yarns are further illustrated in FIG. 6B. The front, back and border yarns are interlaced in a relatively loose pattern having an underlap of at least three needle positions, which are depicted as dots 42. As shown in FIG. 6B, back yarns 34 and front yarns 36 shift diagonally by at least three needle positions in alternating closed-loop interlacing structures. Such a pattern not only provides stretchability to the textile prosthesis 10 but also provides resistance against dilation. Not wishing to be bound by any particular theory, it is believed that the long underlap in the course direction, which is indicated as vector 24, reduces the potential for expansion in the wale direction, which is indicated by vector 28, because the underlap in the course direction inhibits undesirable radial expansion.

To knit textile patterns useful with the present invention, double needle bar warp-knitting machine with multiple beams or guide bars is used to form a flat-knitted seamless tubular structure. A typical guide bar layout is shown in Table 1 below. The guide bars are a combination of ground bars and nested connect bars. The threading pattern for each guide bar is shown below in Table 2 for a 72 needle bifurcated (BIF) tube or body and in Table 3 for a 42 needle straight tube (ST) or leg. The arrangement of each needle for the guide bar is shown below in Tables 4 for a first channel, which is used for a body of a bifurcated tube, and in Table 5 for a second channel, which is used for the legs of a bifurcated tube.

TABLE 1

16 Guide Bar Layout:

| 1 | 2 | 3 | 4 | 5 | 6 | 7 | 8 | 9 | 10 | 11 | 12 | 13 | 14 | 15 | 16 |
|---|---|---|---|---|---|---|---|---|----|----|----|----|----|----|----|
| G | G | 3-C-4 | | 5-C-6 | | 7-C-8 | | 9-C-10 | | 11-C-12 | | 13-C-14 | | G | G |

Notes:
G: Ground Bars
C: Nested Connect Bars

TABLE 2

72 Needle Bifurcated (BIF) Tube or Body
(Y - Threaded / n - Not Threaded Settings)
(One Repeat Unit)

| Bar No. | Note: | | | | | | | | | | | | |
|---------|-------|---|---|---|---|---|---|---|---|---|---|---|---|
| #16 | not used | | n | n | n | n | n | n | n | n | n | n | n |
| #15 | | | n | Y | Y | Y | Y | n | n | Y | Y | Y | Y | n |
| #14 | R | Y | n | n | n | n | n | n | n | n | n | n | Y | Y |
| #13 | CL | | n | n | n | n | n | Y | n | n | n | n | n | n |
| #12 | R | | n | n | n | n | n | n | n | n | n | Y | n | n |
| #11 | CR | | n | n | n | n | n | n | Y | n | n | n | n | n |
| #10 | not used | | n | n | n | n | n | n | n | n | n | n | n | n |
| #9 | not used | | n | n | n | n | n | n | n | n | n | n | n | n |
| #8 | not used | | n | n | n | n | n | n | n | n | n | n | n | n |
| #7 | not used | | n | n | n | n | n | n | n | n | n | n | n | n |
| #6 | CR | | n | n | n | n | n | n | Y | n | n | n | n | n |
| #5 | L | | Y | n | n | n | n | n | n | n | n | n | n | n |
| #4 | CL | n | n | n | n | n | n | Y | n | n | n | n | n | n |
| #3 | L | Y | n | n | n | n | n | n | n | n | n | n | n | n |
| #2 | | | n | n | Y | Y | Y | Y | n | n | Y | Y | Y | Y |
| #1 | not used | | n | n | n | n | n | n | n | n | n | n | n | n |

Notes:
L: left body connect
R: right body connect
CL: left leg connect
CR: right leg connect
Bars 4 and 6 join front bar 2
Bars 11 and 13 join back bar 15
Total needles for BIF is 72 * 2 or 144 needles

TABLE 3

| Bar No. | Note: | ← | | | (One Repeat Unit) | | | | → |
|---|---|---|---|---|---|---|---|---|---|
| | | \multicolumn{8}{c}{42 Needle Straight Tube (ST) or Leg (Y - Threaded / n - Not Threaded Settings)} |
| #16 | not used | n | n | n | n | n | n | n | n |
| #15 | | n | Y | Y | Y | Y | Y | Y | n |
| #14 | R      Y | n | n | n | n | n | n | n | Y |
| #13 | CL | n | n | n | n | n | n | n | n |
| #12 | R | n | n | n | n | n | n | Y | n |
| #11 | CR | n | n | n | n | n | n | n | n |
| #10 | not used | n | n | n | n | n | n | n | n |
| #9 | not used | n | n | n | n | n | n | n | n |
| #8 | not used | n | n | n | n | n | n | n | n |
| #7 | not used | n | n | n | n | n | n | n | n |
| #6 | CR | n | n | n | n | n | n | n | n |
| #5 | L | | Y | n | n | n | n | n | n |
| #4 | CL | n | n | n | n | n | n | n | n |
| #3 | L | Y | n | n | n | n | n | n | n |
| #2 | | n | n | Y | Y | Y | Y | Y | n |
| #1 | not used | n | n | n | n | n | n | n | n |

Notes:
L: left body connect
R: right body connect
CL: left leg connect
CR: right leg connect
Bars 4 and 6 join front bar 2
Bars 11 and 13 join back bar 15
Total needles for ST is (40 for body + 2 for connector) * 2 for total of 84 needles

TABLE 4

Pattern Chains
Top Drum (Body): Channel 1

| Bar #1: | 0-0/0-0// | not used |
|---|---|---|
| Bar #2: | 0_2-0/4-4/4-6/2-2/ | 2-0/4-4/4-6/2-2_0// |
| Bar #3: | 0_4-2/4-4/2-2/2-0/ | 4-2/4-4/2-2/2-0// |
| Bar #4: | 0_2-0/4-4/4-6/2-2/ | 2-0/4-4/4-6/2-2_0// |
| Bar #5: | 0_2-0/2-2/4-4/4-2/ | 2-0/2-2/4-4/4-2_0// |
| Bar #6: | 0_2-0/4-4/4-6/2-2/ | 2-0/4-4/4-6/2-2_0// |
| Bar #7: | 0-0/0-0// | |
| Bar #8: | 0-0/0-0// | |
| Bar #9: | 0-0/0-0// | |
| Bar #10: | 0-0/0-0// | |
| Bar #11: | 0_2-2/4-6/2-2/2-0/ | 2-2/4-6/2-2/2-0// |
| Bar #12: | 0_2-2/2-4/0-2/0-0/ | 2-2/2-4/0-2/0-0// |
| Bar #13: | 0_2-2/4-6/2-2/2-0/ | 2-2/4-6/2-2/2-0// |
| Bar #14: | 0-0/0-2/2-4/2-2/ | 0-0/0-2/2-4/2-2_0// |
| Bar #15: | 0_2-2/4-6/2-2/2-0/ | 2-2/4-6/2-2/2-0// |
| Bar #16: | 0-0/0-0// | not used |

TABLE 5

Pattern Chains
Bottom Drum (Legs): Channel 2

| Bar #1: | 0-0/0-0// | not used |
|---|---|---|
| Bar #2: | 0_2-0/4-4/4-6/2-2/ | 2-0/4-4/4-6/2-2_0// |
| Bar #3: | 0_4-2/4-4/2-2/2-0/ | 4-2/4-4/2-2/2-0// |
| Bar #4: | 0_2-2/4-4/4-6/2-2/ | 2-2/4-4/4-6/2-2_0// |
| Bar #5: | 0_2-0/2-2/4-4/4-2/ | 2-0/2-2/4-4/4-2_0// |
| Bar #6: | 0_2-0/2-2/4-4/4-2/ | 2-0/2-2/4-4/4-2_0// |
| Bar #7: | 0-0/0-0// | |
| Bar #8: | 0-0/0-0// | |
| Bar #9: | 0-0/0-0// | |
| Bar #10: | 0-0/0-0// | |
| Bar #11: | 0_4-2/4-4/2-2/2-0/ | 4-2/4-4/2-2/2-0// |
| Bar #12: | 0_2-2/2-4/0-2/0-0/ | 2-2/2-4/0-2/0-0// |
| Bar #13: | 0_2-2/4-6/2-4/2-2/ | 2-2/4-6/2-4/2-2_0// |
| Bar #14: | 0-0/0-2/2-4/2-2/ | 0-0/0-2/2-4/2-2_0// |
| Bar #15: | 0_2-2/4-6/2-2/2-0/ | 2-2/4-6/2-2/2-0// |
| Bar #16: | 0-0/0-0// | not used |

Figure 7:
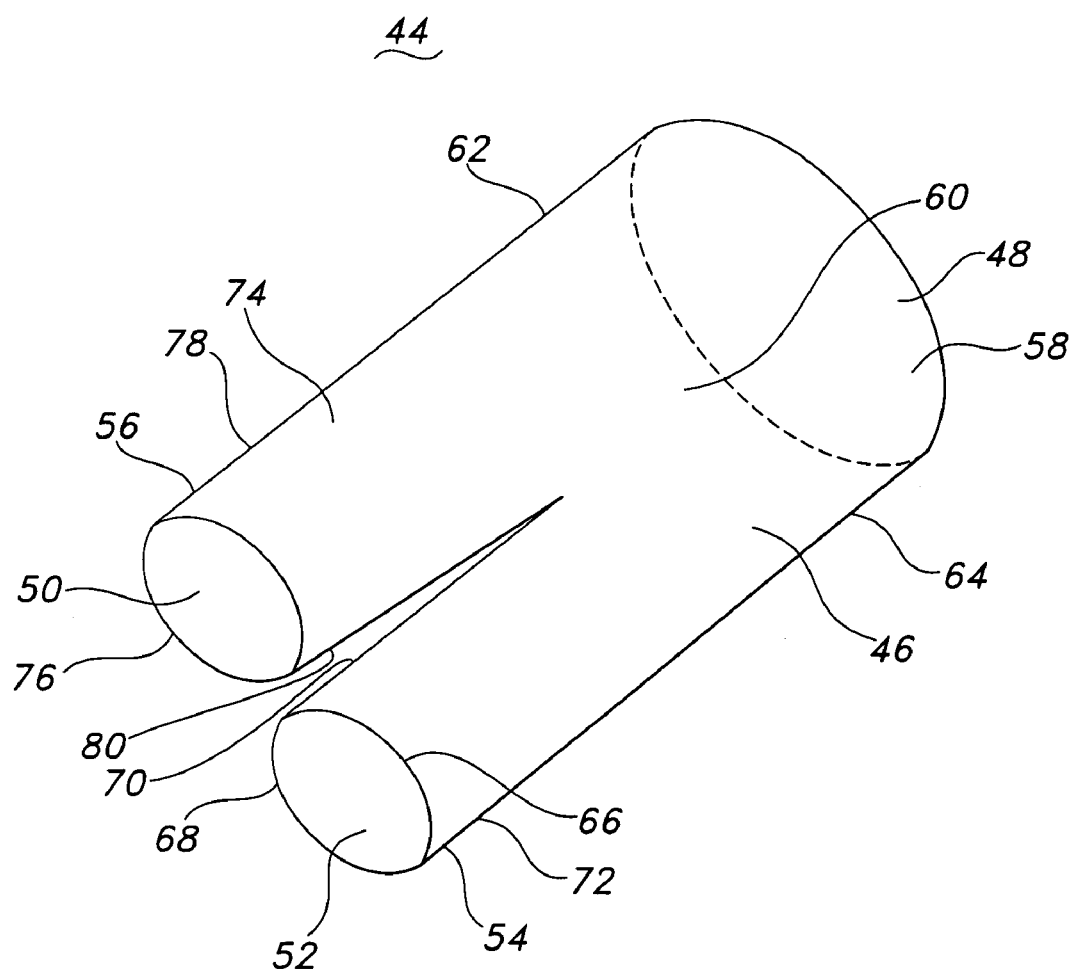
FIG. 7 is a perspective view of a bifurcated prosthesis according to the present invention.

In more detail a bifurcated textile graft 44 is depicted in FIG. 7. The bifurcated textile graft 44 has a main body 46 having an open end 48 and having opposed open ends 52 and 50 of leg A 54 and of leg B 56, respectively. Guide bar #2 is utilized for top or front body portion 58. Guide bar #2 is a ground bar and guide bars #2 and #4 join guide bar #2 to make the top or front body portion 58. Guide bar #15 is utilized for bottom or rear body portion 60. Guide bar #15 is also a ground bar and guide bars #11 and #13 join guide bar #15 to make bottom or rear body portion 60. Guide bars #6 and #13 are utilized for left body portion 62. Guide bars #6 and #11 are utilized for right body portion 64.

Guide bar #2 is utilized for top or front leg portion 66 of leg A 54. Guide bar #15 is utilized for bottom or rear leg portion 68 of leg A 54. Guide bars #6 and #11 are utilized for left leg portion 70 of leg A 54. Guide bars #12 and #14 are utilized for right leg portion 72 of leg A 54.

Guide bar #2 is also utilized for top or front leg portion 74 of leg B 56. Guide bar #15 is also utilized for bottom leg portion 76 of leg B 56. Guide bars #3 and #5 are utilized for left leg portion 78 of leg B 56. Guide bars #4 and #13 are utilized for right leg portion 80 of leg B 56.

The knitted textile graft of the present invention is desirably made on a warp-knitting machine (not shown) using a double needle bar. A useful number of needles per inch for warp knitting is from about 18 to about 36. About 30, or alternatively, about 28 needles per inch are particularly suitable. The trellis of the graft is usually made from a yarn having count from 30 to 300 denier. Desirably, the range of yarn counts for the trellis is from about 30 to about 80. A particularly suitable yarn count is about 40 denier. Moreover, the trellis yarn may be a single ply, a double ply or a multi-ply. The term "multi-ply" is used herein to indicate more than two-ply.

Furthermore, the knitted textile graft of the present invention has greater than 350 stitches per square centimeter, for instance from about 400 to about 1,200 stitches per square centimeter (about 2,600 to about 7,740 stitches per square inch), to provide compliancy of the graft. Desirably, the present invention has from about 800 to about 1,000 stitches per square centimeter (about 5,160 to about 6,500 stitches per square inch). Moreover, the knitted textile graft of the present invention has from about 14 to about 70 courses or wales per centimeter (about 35 to about 160 courses or wales per inch) to provide compliancy of the graft. The number of courses and wales per unit length may be the same or different. Desirably, the present invention has from about 14 to about 25 wales per centimeter (about 35 to about 64 wales per inch). More desirably, the present invention has from about 15.5 to about 17.5 wales per centimeter (about 39 to about 44 wales per inch). Furthermore, the present invention desirably has from about 31 to about 70 courses per centimeter (about 110 to about 160 courses per inch).

In one aspect of the present invention, the knitted textile graft is a knit structure of a single layer with at least a two-needle underlap. Because of the single layer construction the textile wall thickness is minimized to yield a low profile knitted textile graft. The textile wall thickness is from about 0.2 to about 0.4 millimeters. Desirably, the textile wall thickness is from about 0.27 to about 0.31 millimeters. Such thicknesses are measured with a one square inch pressed foot having a seven ounce weight, which results in measuring a one square inch section at a pressure of about 0.44 psi.

Furthermore, the knitted textile graft of the present invention has a burst strength from about 11 $kg/cm^2$ to about 16 $kg/cm^2$ (about 150 psi to about 220 psi). Desirably, the knitted textile graft of the present invention has a burst strength from about 13 kg/cm² to about 14 kg/cm² (about 170 psi to about 190 psi). The stretchability of the knitted textile graft is 50 to 220 percent at a one-kilogram of load. Knitted textile grafts with a stretchability of about 90 to 200 percent at one-kilogram load are also useful. Furthermore, knitted textile grafts with a stretchability of about 120 to 160 percent at one-kilogram load are also useful.

In a typical method of warp knitting the back yarn is fed from two inside beams, each beam being a spool holding a plurality of ends. Outside beams may be used in conjunction with the inside beams; the outside beams being used for feeding the front yarns. Each outside beam also has a plurality of ends. It should be noted, however, that the inside beams may be used for feeding the front yarn and the outside beams used for feeding the back yarn. Regardless of which beams are used, texturized flat yarn is generally used for both the front and back yarns. The minimum number of beams used in making the textile graft of the present invention is 2. A greater number of beams, however, may be found useful for specific applications. About eight to about sixteen guide beams or guide bars have been found to be particularly useful with the practice of the present invention.

Any type of textile product can be used as yarns for the knitted textile graft of the present invention. Of particular usefulness in forming the knitted fabric prosthesis of the present invention are synthetic materials such as synthetic polymers. Synthetic yarns suitable for use in the present invention include, but are not limited to, polyesters, including PET polyesters, polypropylenes, polyethylenes, polyurethanes and polytetrafluoroethylenes. The yarns may be of the monofilament, multifilament, spun type or combinations thereof. The yarns may also be flat, twisted or textured, and may have high, low or moderate shrinkage properties or combinations thereof.

The yarns used in forming the textile grafts of the present invention may be flat, twisted, textured or combinations thereof. Furthermore, the yarns may have high, low or moderate shrinkage properties or combination of different shrinkage properties. Additionally, the yarn type and yarn denier can be selected to meet specific properties desired for the prosthesis, such as porosity and flexibility. The yarn denier represents the linear density of the yarn (number of grams mass divided by 9,000 meters of length). Thus, a yarn with a small denier would correspond to a very fine yarn whereas a yarn with a larger denier, e.g., 1000, would correspond to a heavy yarn. The yarns used with the present invention may have a denier from about 20 to about 200, preferably from about 30 to about 100. Preferably, the yarns are polyester, such as polyethylene terephthalate (PET), and more preferably the yarns are one ply, 40 denier, 27 filament flat and texturized polyester yarns. Additionally, one ply, 50 denier, 48 filament flat polyester yarns are also useful.

After knitting the textile graft of the present invention is optionally cleaned or scoured in a basic solution of warm water, e.g., about 50° C. to about 65° C. (about 120° F. to about 150° F.), and detergent. The textile is then rinsed to remove any remaining detergent.

After the textile graft is optionally scoured, the graft is compacted or shrunk to reduce and control, in part, the porosity of the graft. Porosity of a knitted material is measured on the Wesolowski scale and by the procedure of Wesolowski. In the Wesolowski test, a fabric test piece is clamped flatwise and subjected to a pressure head of about 120 mm. of mercury. Readings are obtained which express the number of millimeters of water permeating per minute through each square centimeter of fabric. A zero reading represents absolute water impermeability and a value of about 20,000 represent approximate free flow of fluid.

The porosity of the textile graft 12 is often from about 7,000 to about 15,000 on the Wesolowski scale after being knitted on the double needle bar Raschel knitting machine. A more desirable porosity is from about 30 to about 5,000 on the Wesolowski scale and textile graft is compacted or shrunk in the wale direction to obtain the desired porosity. A solution of an organic component, such as hexafluoroisopropanol or trichloroacetic acid, and a halogenated aliphatic hydrocarbon, such as methylene chloride, is used to compact the textile graft by immersing it into the solution for up to 30 minutes at temperatures from about 15° C. to about 160° C. Other compacting solutions may suitably be used, such as those disclosed in U.S. Pat. Nos. 3,853,462 and 3,986,828, whose contents are incorporated by reference herein.

FIG. 8 depicts a cross-sectional view of textile prosthesis 10 having a flat width of $W_0$. As depicted in FIG. 9, if textile prosthesis 10 were placed on a cylindrical mandrel (not shown) without any stretching of the prosthesis or without force otherwise applied to force it over the mandrel, the textile prosthesis 10 would have a circular diameter of $D_0$. As $W_0$ approximately represents half of circumference of the circle in FIG. 9, the circular diameter, $D_0$, is approximated by the formula of $D_0 = 2W_0/\pi$.

To reorient the radially extending yarns, or course yarns, of the textile prosthesis 10, the prosthesis is placed on a mandrel that is from about 1.5 to about 3.0 times larger than the corresponding flat-knitted diameter $D_0$. As depicted in FIG. 10, the textile prosthesis 10 is disposed over a mandrel 82. Mandrel 82 has an external diameter of $D_1$, which is depicted as being approximately 2.4 times larger than the $D_0$ depicted in FIG. 9.

Figure 11A:
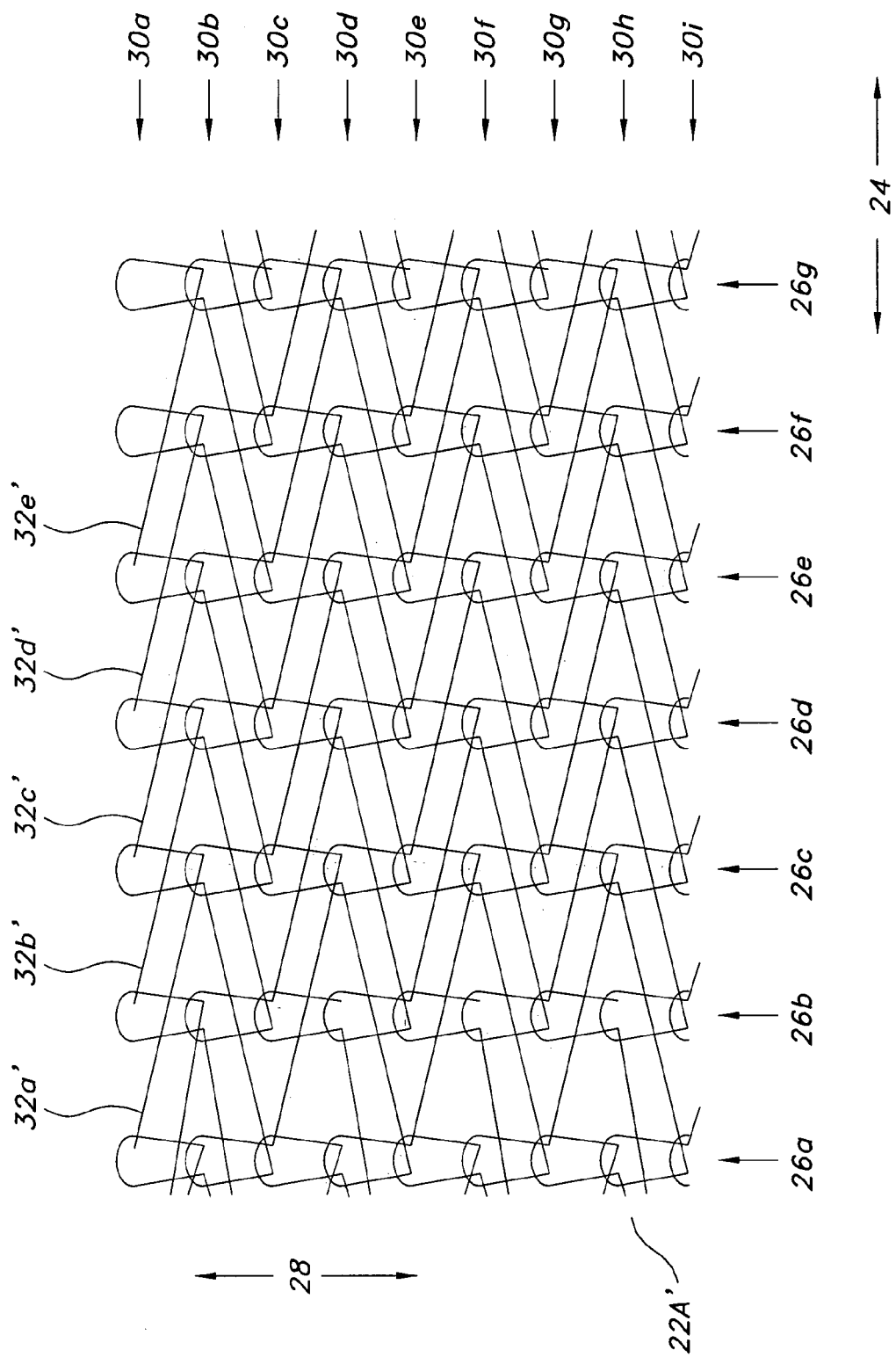
FIGS. 11A and 11B are illustrations of the reoriented yarns patterns of FIGS. 4A and 4B, respectively.
Figure 11B:
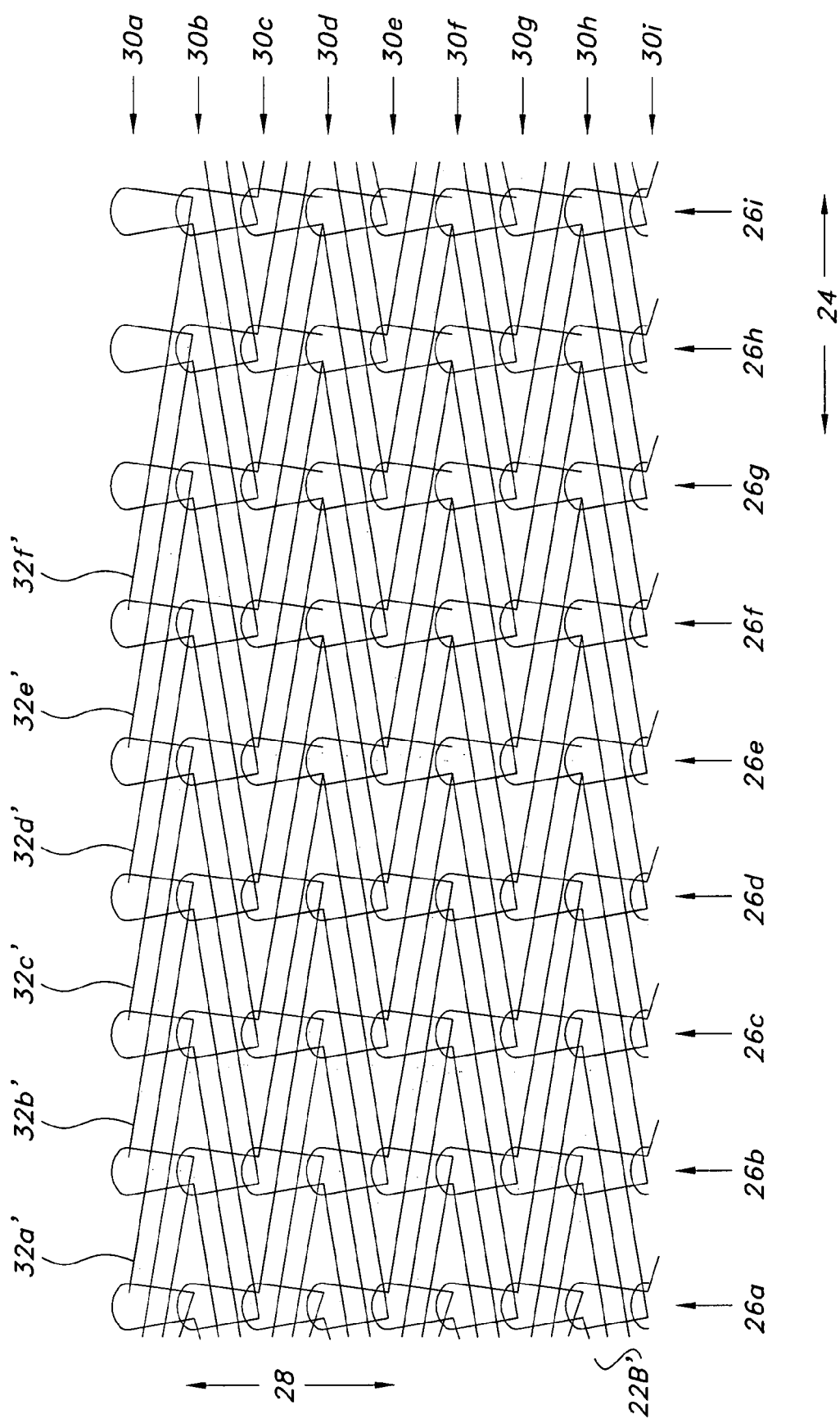

Such a placement of the textile prosthesis 10 over mandrel 82 reorients the yarns as depicted in FIGS. 11A and 11B to provide the textile prosthesis 10'. As depicted in FIG. 11A, the two needle underlap textile portion 22A of FIG. 4A is reoriented to provide a reoriented two needle underlap textile portion 22A'. Similarly, as depicted in FIG. 11B, the three needle underlap textile portion 22B of FIG. 4B is reoriented to provide a reoriented two needle underlap textile portion 22B'. In FIGS. 11A and 11B the radially extending course yarns 32a', 32b', 32c', 32d' and 32e have been reoriented from their flat knitted orientation to a stretched orientation where the radially extending course yarns 32a', 32b', 32c', 32d' and 32e' are disposed in a more parallel extending fashion to the radial or circumferential axis of the textile prosthesis 10'. Such rearrangement or reorientation is schematically depicted in FIGS. 12 and 13.

FIG. 12 depicts radially extending yarn 32a as being disposed by an acute angle of $\beta_0$ from the radial or circumferential axis C of the textile prosthesis 10. FIG. 13 depicts reoriented radially extending yarn 32a' as being disposed by an acute angle of $\beta_1$ from the radial or circumferential axis C of the textile prosthesis 10 after placement of the textile prosthesis 10 onto mandrel 82. For the high stretch knit patterns of the present invention, i.e. the two or three needle underlap with a one needle overlap, the acute angle, $\beta_1$, after reorientation is significantly smaller than the acute angle, $\beta_0$, before orientation. Correspondingly, the radially extending yarns are reoriented from a flat-knitted or first obtuse angle, $\theta_0$, from the lengthwise direction, L, of the prosthesis 10 to a reoriented or second and larger obtuse angle, $\theta_1$.

Mandrels useful with the present invention are depicted in FIGS. 14A to 15B. As depicted in FIGS. 14A and 14B, mandrel 84 is a straight tubular member having opposed ends 86 and 88. Desirably, one end 88 is rounded, as depicted in FIG. 14B, to facilitate placement of a prosthesis or graft thereover. Although mandrel 84 is depicted as a substantially straight tubular member, mandrels of the present invention are not so limited. For example, mandrel 84 may be flared (not shown) or have a varying diameter (not shown) to provide shaped grafts. Further multiple lumen mandrels, such as bifurcated mandrel 90, are useful with the present invention. As depicted in FIG. 15A and 15B, bifurcated mandrel 90 desirably has two rounded ends 92 and 94 for placement of a bifurcated graft (not shown) thereover.

As noted above, preferably the tubular-knitted graft of the present invention is constructed of polyester which is capable of shrinking during a heat-set process. For instance, such grafts are typically flat-knitted in a tubular form. Due to the nature of the flat-knitting process, the tubular graft is generally flat in shape after knitting. Such grafts, however, when constructed of shrinkable polyester yarn, can be heat set on a mandrel to form a generally circular shape.

Such a heat-setting process is accomplished by first knitting the graft in a seamless tubular form out of a material capable of shrinking during a heat-setting or similar process. The graft may be preshrunk before it is placed on a mandrel. Preshrinking may be achieved by submitting the woven graft to moderate temperatures, such as from about 90° C. to about 205° C. (about 190° F. to about 400° F.). Usually the graft is placed in a medium for the preshrinking. Such a medium can include without limitation hot water, a chemical fluid, such as methylene chloride, or a gas, such as air or carbon dioxide. The graft of the present invention, however, may suitably be made without such a preshrinking of the yarns.

After the graft is knitted or alternatively knitted and preshrunk, the graft is placed on a mandrel, and heated in an oven at a temperature and time capable of causing the yarns of the graft to heat set to the shape and diameter of the mandrel. Preferably polyester yarns are used, and the heat setting is accomplished at time and temperatures appropriate for the material. For example, heat setting can be accomplished at about 90° C. to about 225° C. (about 190° F. to about 437° F.) for a period of about less than an hour. Temperatures in the range of about 130° C. to about 220° C. (about 260° F. to about 428° F.) are also useful. Desirably, temperatures from about 150° C. to about 215° C. (about 300° F. to about 419° F.) are also useful. Desirably, time periods from about 5 to about 30 minutes are useful. More desirably, with time periods from about 10 to about 20 minutes are useful. Other methods of heat setting known in the art may be employed. After such a heat setting process, the graft can be formed into a shape desired for implantation, having a generally circular inner lumen.

Knitting patterns useful with the present invention include conventional warp-knitted patterns and high-stretch, warp-knitted patterns. Commonly used warp-knitted patterns include locknit (also referred to as tricot or jersey knits), reverse locknit, sharkskin, queenscord and velour knits. Useful high stretch, warp-knitted patters include those with multiple patterns of diagonally shifting yarns, such as certain modified atlas knits which are described in U.S. Pat. No. 6,540,773, the contents of which are in incorporated herein by reference. Other useful high-stretch, warp knitted patterns include the above-described patterns with multiple needle underlap and one needle overlap which are further described in U.S. Pat. No. 6,554,855 and U.S. patent application Publication No. 2003/0204241 A1, the contents of which are incorporated herein by reference.

Figure 16A:
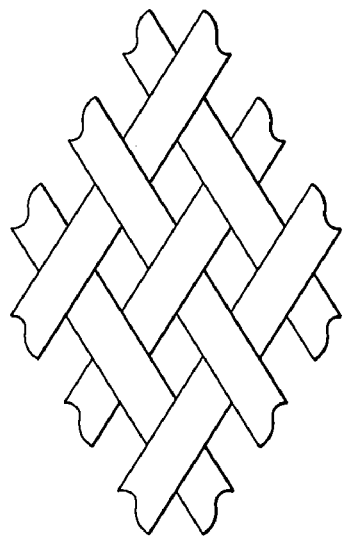
FIGS. 16A through 16C depict braided patterns useful with the practice of the present invention.
Figure 16B:
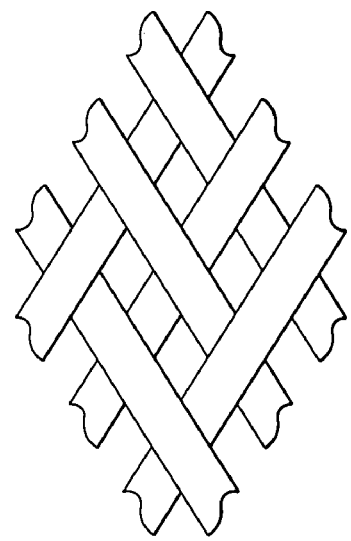
Figure 16C:
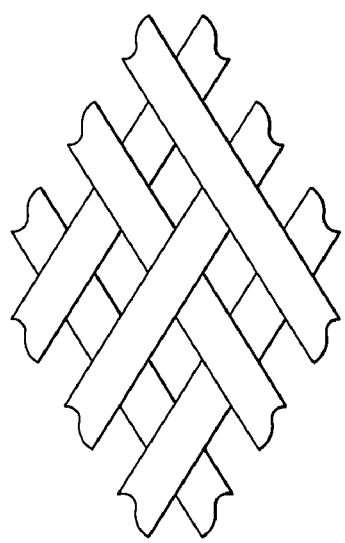

Further, the graft or prosthesis of the present invention is not limited to a knitted textile. For example, any textile pattern or construction having radially extending yarns capable of being reoriented by the methods of the present invention may suitably be used. For example, braiding may also be used. As depicted in FIGS. 16A through 16C braiding of yarns includes the interlacing of at least two yarn systems such that the paths of the yarns are diagonal to the fabric delivery direction, forming either a flat or tubular structure. Useful braids include, but are not limited to, a diamond braid 96 having a 1/1 intersection repeat as shown in FIG. 16A, a regular braid 98 having a 2/2 intersection repeat as shown in FIG. 16B, or a Hercules braid 100 having a 3/3 intersection repeat as shown in FIG. 16C. Moreover, a triaxial braid may also be used. A triaxial braid, not shown, has at least one yarn that typically runs in the longitudinal direction or axial direction of the textile portion to limit yarn movement. The axial or longitudinal yarn is not interlaced or interwound with the other braid yarns, but is trapped between the different sets of yarns in the braided structure. Moreover, an interlocking three-dimensional braided structure or a multi-layered braided structure is also useful. A multi-layered braided structure is defined as a structure formed by braiding wherein the structure has a plurality of distinct and discrete layers. These layers may be bound by interlocking yarns or by adhesive laminates, sewing or the like.

Generally, a braided structure is formed having a braid angle from about 54.5° to about 90° with respect to the longitudinal axis of the braided structure, desirably about 54.5° to about 75°. The yarns of the braid tend to seek equilibrium at a braid angle of about 54.5°, which is a neutral angle for tubular vessels under pressure. Thus, when the braid angle is larger than the neutral angle, when pressure is exerted from within, for example due to fluid flow, the yarns will tend to scissor and decrease the braid angle thereby elongating or stretching the braided structure in order to reach the neutral angle.

Various stent types and stent constructions may be employed in the invention. Useful stents include, without limitation, self-expanding stents and balloon expandable stents. The stents may be capable of radially contracting or expanding, as well, and in this sense can be best described as radially or circumferentially distensible or deformable. Self-expanding stents include those that have a spring-like action which causes the stent to radially expand, or stents which expand due to the memory properties of the stent material for a particular configuration at a certain temperature. Nitinol is one material which has the ability to perform well while both in spring-like mode, as well as in a memory mode based on temperature. Other materials are of course contemplated, such as stainless steel, platinum, gold, titanium and other biocompatible metals, as well as polymeric stents.

Figure 17:
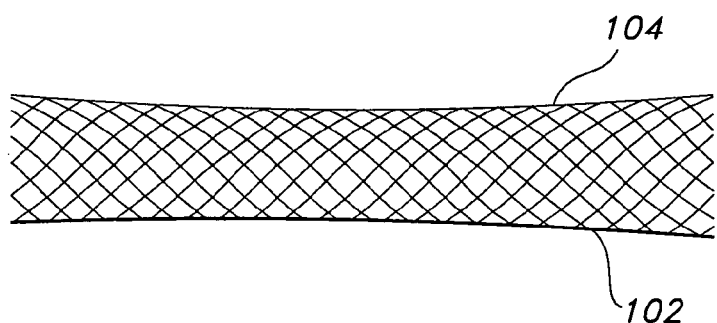
FIG. 17 is a longitudinal view of a wire stent of the present invention.

The configuration of a stent or a bifurcated stent may be of any suitable geometry. As shown in FIG. 17, wire stent 102 is a hollow tubular structure formed from wire strand 104 or multiple wire strands. Wire stent 102 may be formed by, for example, braiding or spinning wire strand(s) 104 over a mandrel (not shown). Wire stent 102 is capable of being radially compressed and longitudinally extended for implantation into a bodily lumen. The degree of elongation depends upon the structure and materials of the wire stent 102 and can be quite varied, for example, about 50% to about 200% of the length of wire stent 102. The diameter of wire stent 102 may also become several times smaller as it elongates. Desirably, stents that have substantial dimensional variations are wire stents. Unitary stent structures may be obtained by braiding and/or filament winding stent wires to obtain complex stent geometries, including complex stent geometries, including complex bifurcated stents. Alternatively, stent components of different sizes and/or geometries may be mechanically secured by welding or suturing. Additional details of wire stents of complex geometry are described in U.S. Pat. Nos. 6,325,822 and 6,585,758, the contents of which are incorporated herein by reference.

Figure 18:
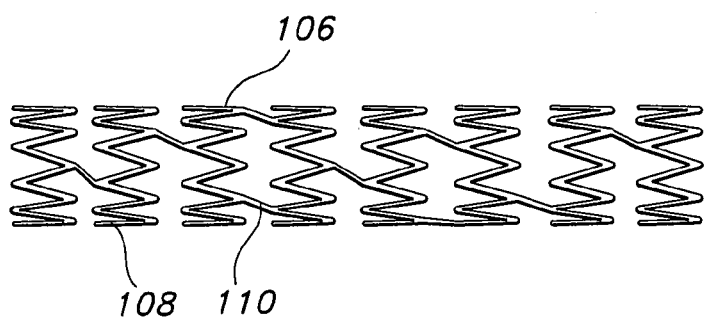
FIG. 18 is a longitudinal view of a zig-zag stent of the present invention.

A zig-zag wire stent 106 is also useful. Wire strand 108 is being arranged in what can be described as a multiple of "Z" or a "zig-zag" patterns to form a hollow tubular stent. The different zig-zag patterns may optionally be connected by connecting member 110. Further, zig-zag wire stent 106 is not limited to a series of concentric loops as depicted in FIG. 18, but may be suitably formed by helically winding of the "zig-zag" pattern over a mandrel (not shown).

Figure 19:
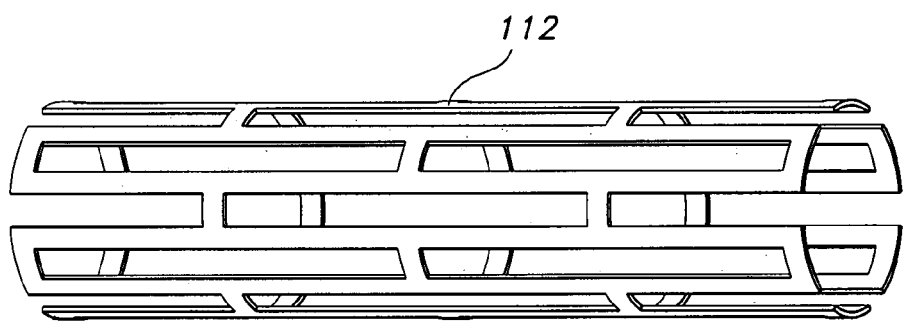
FIG. 19 is a perspective view of a slotted stent of the present invention.

A slotted stent 112 is also useful. As depicted in FIG. 19, slotted stent 112 is suitably configured for implantation into a bodily lumen (not shown). Upon locating the slotted stent 112 at the desired bodily site, slotted stent 112 is radially expanded and longitudinally contracted for securement at the desired site.

Figure 20:
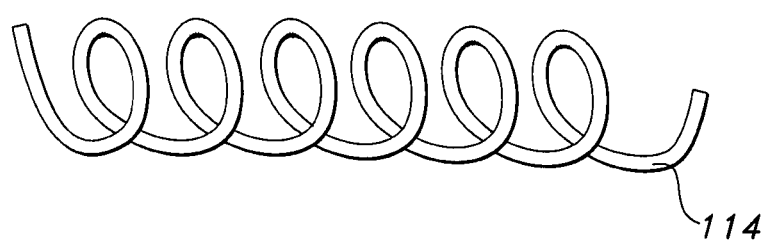
FIG. 20 is a perspective view of a helical coil stent formed of a single wound wire according to the present invention.
Figure 21:
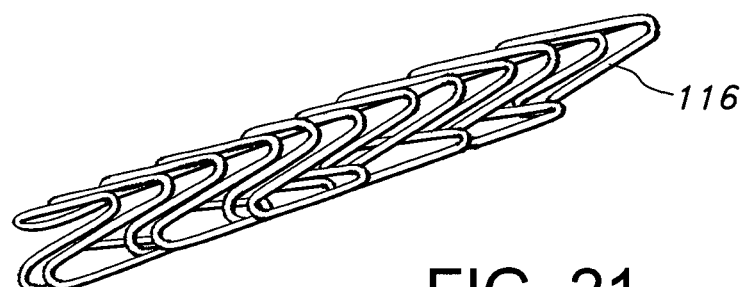
FIG. 21 is a perspective view of a stent having an elongate nested helically coiled configuration according to the present invention.

Other useful stents capable of radial expansion are depicted in FIGS. 20 and 21. As depicted in FIG. 20, stent 114 is a helical coil which is capable of achieving a radially expanded state (not shown). Stent 116, as depicted in FIG. 21, has an elongate pre-helically coiled configuration as shown by the waves of non-overlapping undulating windings. These helically coiled or pre-helically stents, commonly referred to as nested stents, are also useful with the practice of the present invention.

Figure 22:
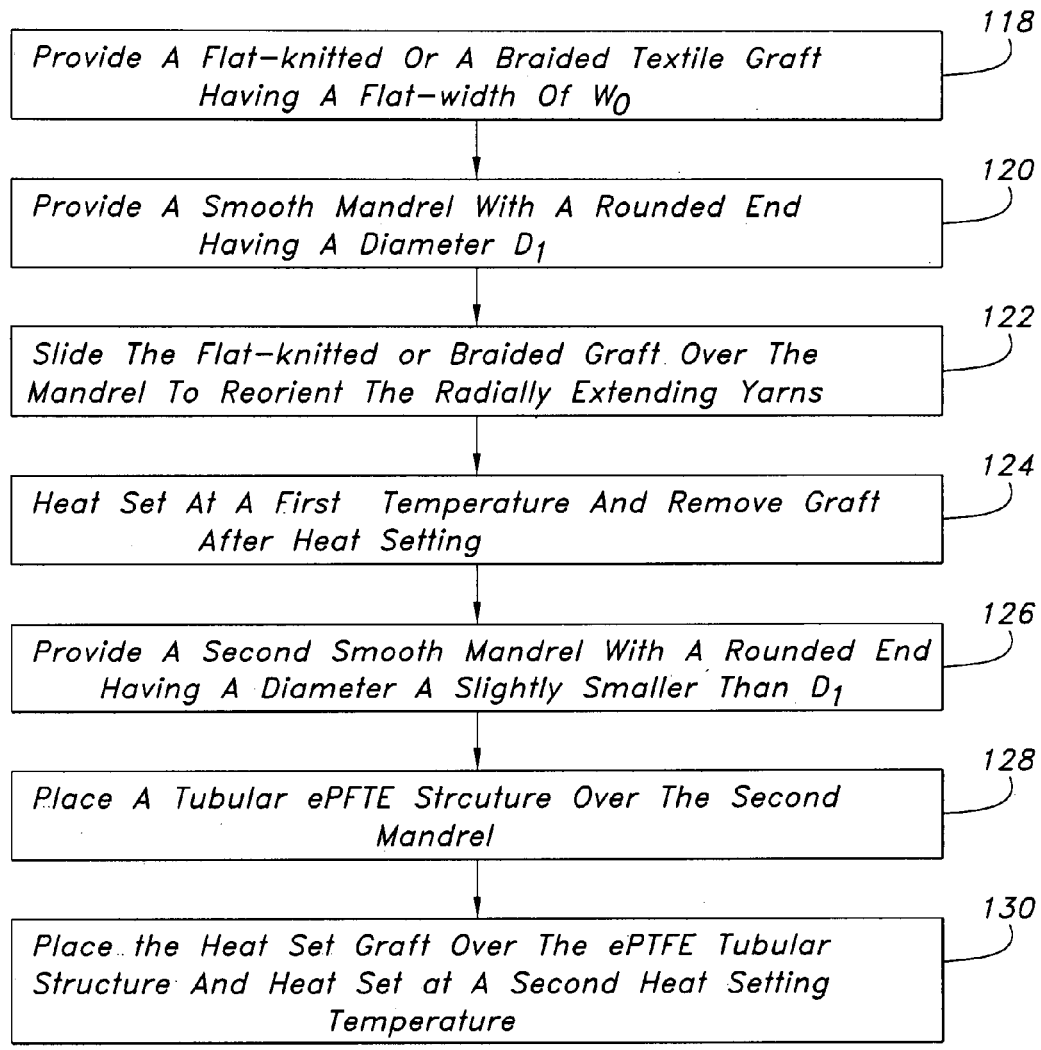
FIG. 22 is a schematic of a method according to an aspect of the present invention.

In one aspect of the present invention, as depicted in FIG. 22, a method for reorienting radially extending yarns is provided. At step 118, a flat-knitted or braided textile graft is provided having a flat-width of $W_0$. At step 120, a smooth mandrel with at least one rounded end is provided. The mandrel has a diameter which is typically greater than the corresponding graft diameter by at least a factor of 1.5, for example from about 1.5 to about 3.0 times larger than the initial graft diameter ad knitted or braided. At step 122, the radially extending yarns are reoriented by sliding the graft over the mandrel. When the high-stretch knitted grafts of the present invention are slid over the mandrel, the radially extending yarns are reoriented without substantially changing the length of the graft. At step 124, the graft is heat set. Desirably, the heat set is done at a temperature from about 120° C. to about 215° C. for about 5 to about 15 minutes, more desirably, from about 120° C. to about 190° C. This heat set fixes the radially extending yarns in a reoriented pattern and also sets the graft at the diameter, $D_1$, of the mandrel.

In another aspect of the present invention, a tubular medical device, such as textile prosthesis 10, is provided. The device includes a graft having opposed open ends and a textile wall extending in a lengthwise direction therebetween defining a graft diameter. The textile wall includes radially extending yarns selectively inter-knitted with longitudinally extending yarns to define a knitted textile pattern with a one needle overlap and a two needle or greater underlap. The graft has a wall thickness of less than about one millimeter, desirably less than about 0.4 millimeters, and expands less than 15 in diameter when subjected to normal physiological pressures within body lumens. The graft may further include a stent circumferentially disposed about an interior portion of the textile wall or an exterior portion of the textile wall. Additionally, the graft may further include a tubular layer or sheet of expanded polytetrafluoroethylene circumferentially disposed about an interior portion of the textile wall or an exterior portion of the textile wall. Furthermore, the graft may further include a stent circumferentially disposed about the interior portion or the exterior portion of the textile wall or about an interior portion or an exterior portion of the expanded polytetrafluoroethylene. Desirably, the graft expands less than 10 percent in diameter when subjected to an internal pressure of about 120 mm Hg. More desirably, the graft expands less than 7 percent in diameter when subjected to an internal pressure of about 120 mm Hg. Such pressures exceed normal physiological pressures within body lumens. For example, the mean aortic pressure is about 95 mm Hg in a normal individual. At high pulse rates the mean arterial pressure can be approximated by the arithmetic average of the systolic and diastolic pressures. At low or normal resting heart rates the mean arterial pressure can be approximated by the arithmetic sum of the diastolic pressure plus one-third of the difference between the systolic and diastolic pressures. Such approximations are used because the cardiac output is intermittent and the pressure is pulsatile. Further, grafts positioned for aneurysm repair are also subjected to a back pressure of the vessel wall at or near the aneurysm. Such back pressure is typically from about 20 to about 50 mm HG. Thus, the dilation test results in Examples 7 and 8, which are described below, and the internal pressures described above are higher than normal physiological dilation pressures that a graft would experience within body lumens because the associated back pressures.

Desirably, the improved dilation properties for the textile grafts of the present invention are achieved without increasing the overall profile of the graft. For example, the grafts of the present invention have improved resistance to dilation without the use of reinforcement members, such as filament or strand (i.e., polymeric, textile, metallic, etc.) support members which may be helically, radially, longitudinally, or otherwise disposed onto the graft, or other support members, such as stents. Further, the grafts of the present invention exhibit the improved dilation resistance without the use of reinforcement yarns or strands, such as metallic strands or yarns or monofilament yarns, for example polypropylene, within the textile pattern which differ from other yarns, such as but not limited to polyester, including polyethylene terephthalate.

If a layer of ePTFE is to be secured to the graft, then additional processing steps are described below. At step 126, a second mandrel is provided which has a diameter slightly smaller that the diameter of the first mandrel. Desirably, the diameter of the second mandrel is from about 0.5 mm to about 1.0 mm smaller than the diameter of the first mandrel. At step 128, a tubular layer or sheet of ePTFE is placed over the mandrel. After applying adhesive, such as Corethane®, to either or both the ePTFE and the graft, the graft from step 124 is then placed over the ePTFE. The textile graft and the ePTFE are then subjected to another heat setting temperature for about 5 to about 15 minutes. Desirably, the second heat setting temperature is from about 10° C. to about 20° C. higher than the first heat setting temperature of step 124. Preferably, the second heat setting temperature is from about 175° C. to about 215° C.

Stent-graft composite devices are also contemplated having self-expanding stents and balloon expandable stents. Self-expanding stents include those that have a spring-like action which causes the stent to radially distend, i.e., expand and/or contract, or stents which expand due to the memory properties of the stent material for a particular configuration at a certain temperature. Balloon expandable stents require an applied force, typically from an expandable balloon on a catheter, to radially distend.

One type of polymeric or non-textile material particularly useful is polytetrafluoroethylene (PTFE). PTFE exhibits superior biocompatibility and low thrombogenicity, which makes it particularly useful as vascular graft material in the repair or replacement of blood vessels. Desirably the non-textile layer is a tubular structure manufactured from expanded polytetrafluoroethylene (ePTFE). The ePTFE material has a fibrous state which is defined by interspaced nodes interconnected by elongated fibrils. The space between the node surfaces that is spanned by the fibrils is defined as the internodal distance. When the term expanded is used to describe PTFE, it is intended to describe PTFE which has been stretched, in accordance with techniques which increase the internodal distance and concomitantly porosity. The stretching may be in uni-axially, bi-axially, or multi-axially. The nodes are spaced apart by the stretched fibrils in the direction of the expansion.

Desirably, the ePTFE material is a physically modified ePTFE tubular structure having enhanced axial elongation and radial expansion properties of up to 600 percent by linear dimension. The physically modified ePTFE tubular structure is able to be elongated or expanded and then returned to its original state without an elastic force existing therewithin. Such a physically modified ePTFE tubular structure is advantageously used in conjunction the devices of the present invention.

One example of a physically modified ePTFE tubular structure is one that has circumferentially oriented nodes and longitudinally traversing fibrils, where the fibrils have been hingeably rotated to provide for the enhance expansion properties. Additional details of the physically modified ePTFE and methods for making the same can be found in commonly assigned application titled, "ePTFE Graft With Axial Elongation Properties", assigned U.S. application Ser. No. 09/898,415, filed on Jul. 3, 2001, published on Jan. 9, 2003 as U.S. application Publication No. 2003/0009210 A1, the contents of which are incorporated by reference herein.

Figure 23:
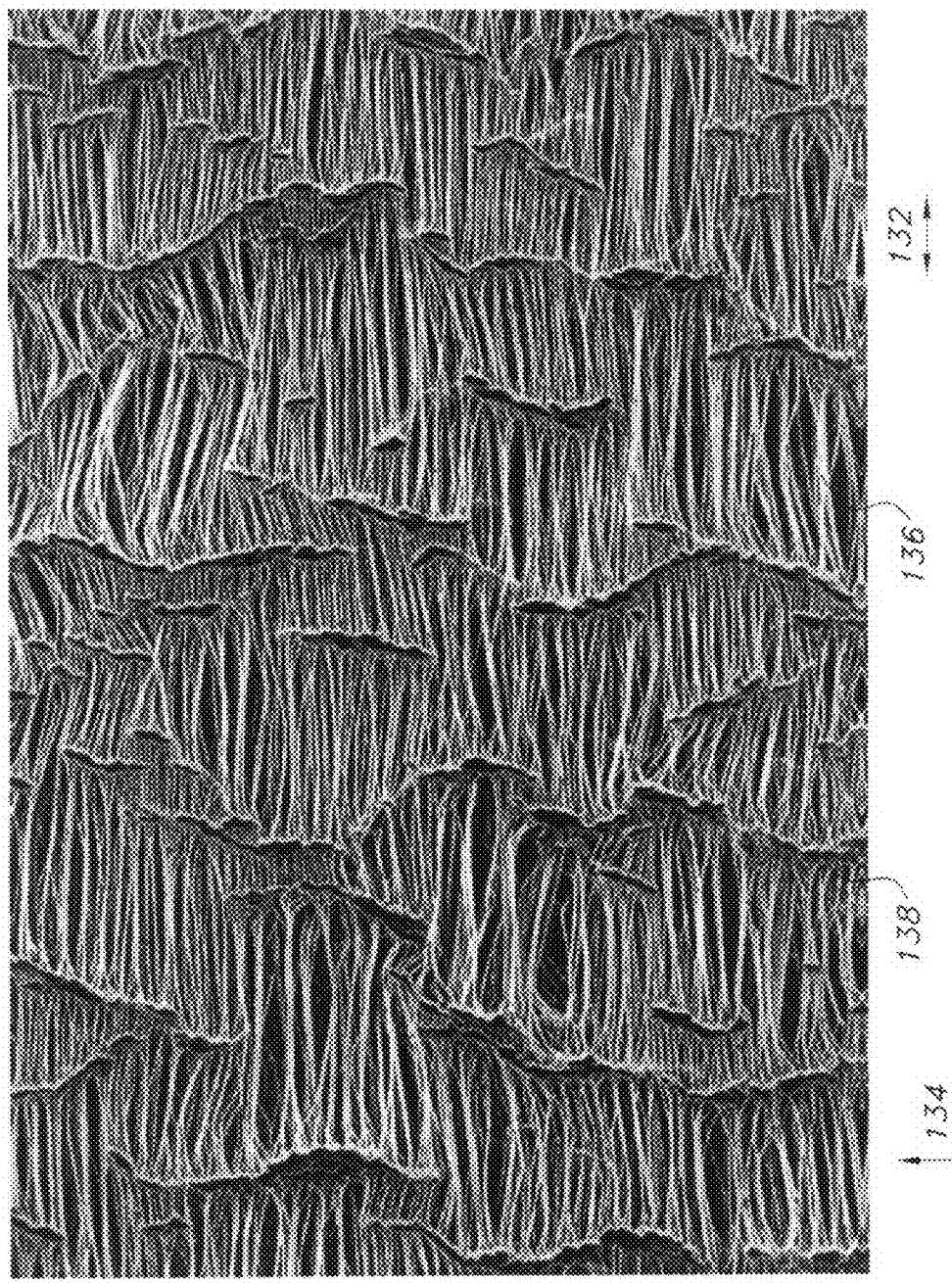
FIG. 23 is a photomicrograph showing a longitudinally expanded ePTFE structure.

FIG. 23 is a photomicrograph of a traditionally longitudinally expanded ePTFE tubular structure. The tube has been stretched in the longitudinal direction shown by directional arrow 132, leaving the nodes circumferentially oriented in circumferential direction shown by the directional arrow 134. The fibrils 136 are shown as being uniformly oriented in the longitudinal direction shown by directional arrow 132. Nodes 138 are shown and are uniformly oriented in circumferential direction 134.

Figure 24:
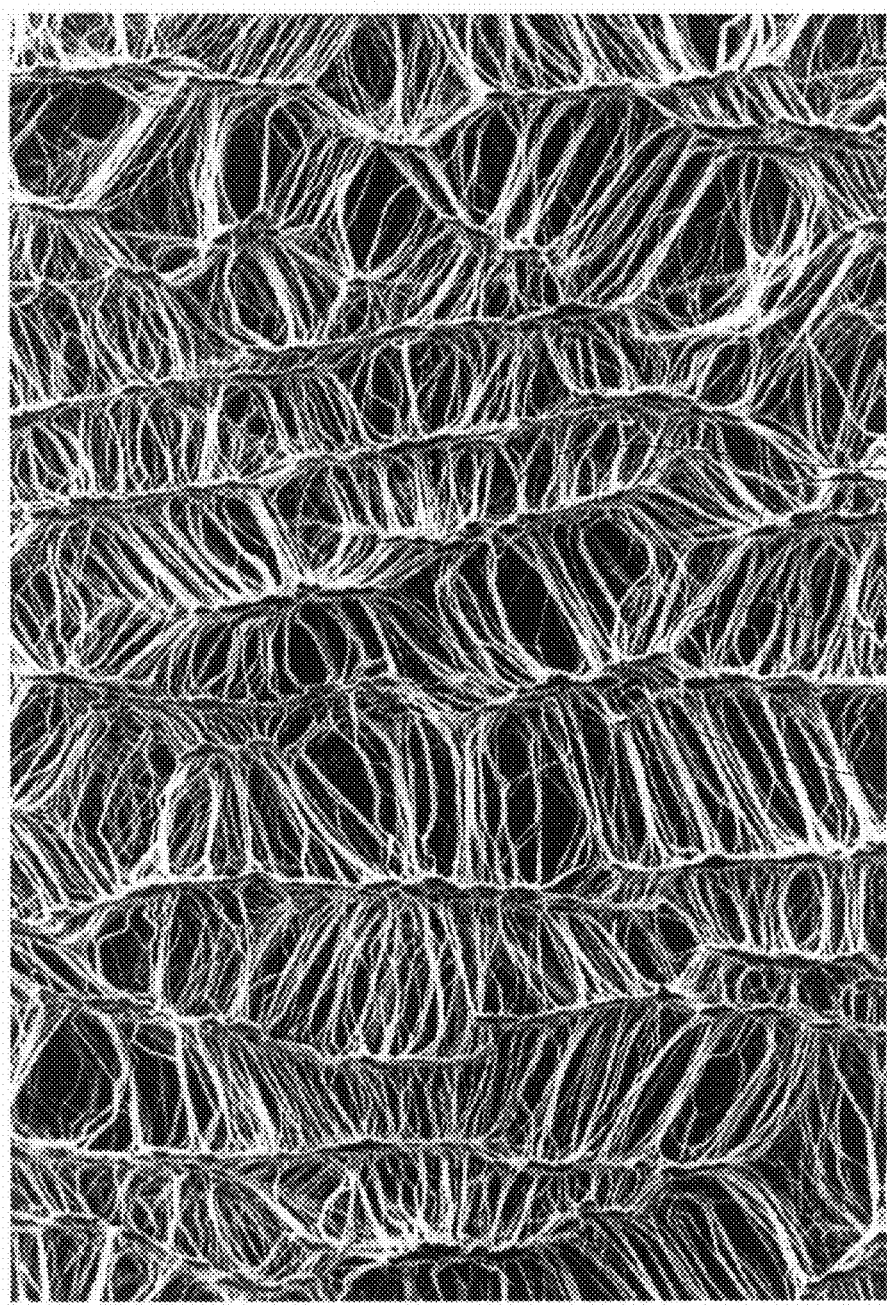
FIG. 24 is a photomicrograph of physically modified ePTFE structure having enhanced elongation properties as compared to the ePTFE structure of FIG. 23.

FIG. 24 is a photomicrograph of the physically modified ePTFE tubular structure having circumferentially oriented nodes and longitudinally traversing fibrils. Nodes 140 are shown in the photomicrograph with a set of fibrils with first ends 142 and second ends 144 attached thereto. The fibrils with first ends 142 and second ends 144 are shown in a hingeably rotated position so that they are not substantially longitudinally oriented in the direction shown by directional arrow 132 as compared to the substantially longitudinally oriented parallel fibril structures 136 of FIG. 23. The term "hingeably rotated" and variants thereof refer to reorientation of previously uniformly oriented line segments by a change in position of one end of each line segment in relation to the other end of each segment, which remains fixed; i.e., the "hinge" about which the other end rotates. The reorientation takes place without a substantial change in dimension of the line segment. Additional details of the physically-modified ePTFE and methods for making the same can be found in commonly assigned application titled, "ePTFE Graft With Axial Elongation Properties", assigned U.S. application Ser. No. 09/898,415, filed on Jul. 3, 2001, published on Jan. 9, 2003 as U.S. application Publication No. 2003/0009210 A1, the contents of which are incorporated by reference herein.

The bonding agent may include various biocompatible, elastomeric bonding agents such as urethanes, styrene/isobutylene/styrene block copolymers (SIBS), silicones, and combinations thereof. Other similar materials are contemplated. Desirably, the bonding agent may include polycarbonate urethanes sold under the trade name CORETHANE®. This urethane is provided as an adhesive solution with preferably 7.5% Corethane, 2.5 W30, in dimethylacetamide (DMAc) solvent.

A composite textile graft and non-textile layer, is desirably formed as follows. A thin non-textile, such as PTFE or ePFTE, tube is formed in a conventional forming process such as by tubular extrusion or by sheet extrusion where the sheet is formed into a tubular configuration. The non-textile tube is placed over a stainless steel mandrel (not shown) and the ends of the tube are secured. The non-textile tube is then spray coated with an adhesive solution, for example from about 1% to about 15% Corethane® urethane range, 2.5 W30 in DMAc. The coated non-textile tube is placed in an oven heated in a range from 18° C. to 215° C. for 5 minutes to overnight to dry off the solution. If desired, the spray coating and drying process can be repeated multiple times to add more adhesive to the non-textile tube. The coated non-textile tube is then covered with the textile graft to form a composite prosthesis. One or more layers of elastic tubing, preferably silicone, are then placed over this composite structure. This holds the composite structure together and assures that complete contact and adequate pressure is maintained for bonding purposes. The assembly of the composite graft within the elastic tubing is placed in an oven and heated in a range of 180° C. to 220° C. for approximately 5 to 30 minutes to bond the layers together. Additional details relating to useful bonding agents and their application to textile and non-textile surfaces may be found in U.S. application Ser. No. 10/167,676, filed Jun. 11, 2002, published on Jan. 23, 2003 as U.S. patent application Publication No. 2003/0017775, and in U.S. application Ser. No. 10/166,842, filed Jun. 11, 2002, published on Jul. 24, 2003 as U.S. patent application Publication No. 2003/0139806, both of which are entitled "Composite ePTFE/Textile Prosthesis" and both of which are incorporated herein by reference.

Figure 25:
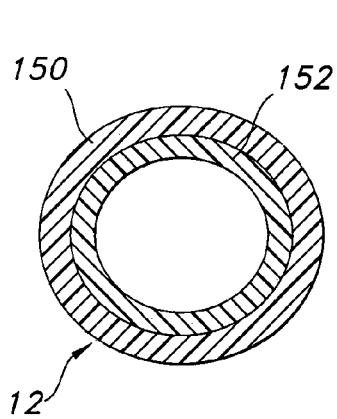
FIG. 25 is a cross sectional view of the prosthesis of the present invention depicting a tubular wall having a textile outer wall portion and a polymeric inner layer wall portion.
Figure 26:
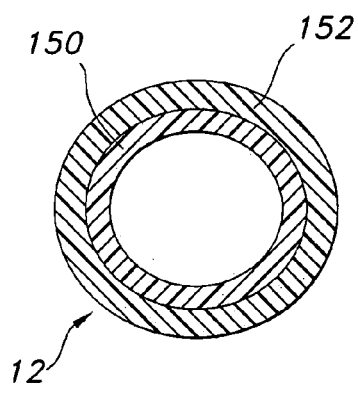
FIG. 26 is a cross sectional view of the prosthesis of the present invention depicting a tubular wall having a textile inner wall portion and a polymeric outer layer wall portion.
Figure 27:
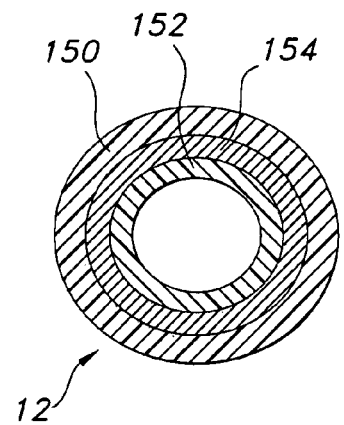
FIG. 27 is a cross sectional view of the prosthesis of the present invention depicting a tubular wall having a textile outer wall portion, a polymeric inner layer wall portion, and a stent disposed therebetween.
Figure 28:
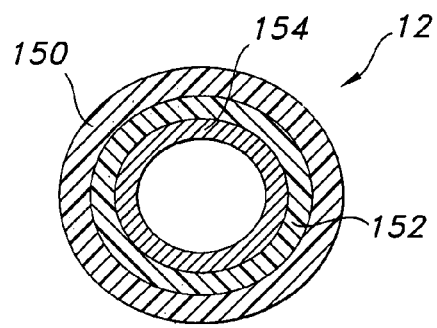
FIG. 28 is a cross sectional view of the prosthesis of the present invention depicting a tubular wall having a textile outer wall portion, a polymeric inner layer wall portion, and a stent disposed on the inner surface of the polymeric inner layer.
Figure 29:
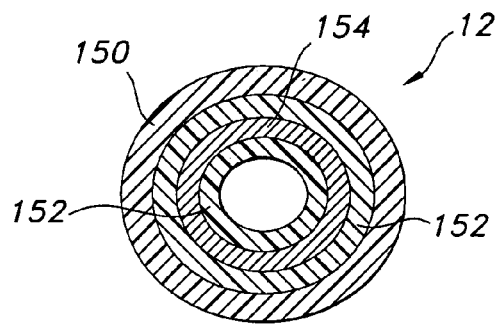
FIG. 29 is a cross sectional view of the prosthesis of the present invention depicting a tubular wall having a textile outer wall portion and a stent having interior and exterior polymeric wall portions.
Figure 30:
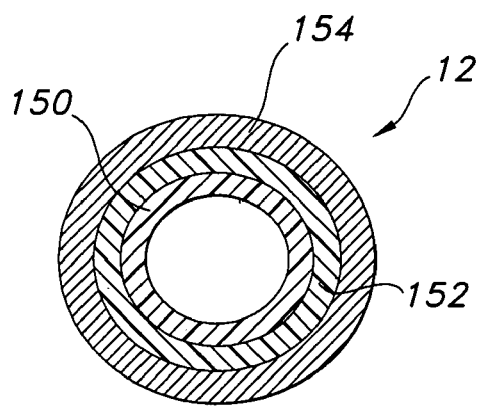
FIG. 30 is a cross-sectional view of the prosthesis of the present invention depicting a tubular wall having an exterior stent portion with a polymeric inner layer portion disposed on the inner surface of the stent and a textile inner wall portion disposed on the interior surface of the polymeric portion.
Figure 31:
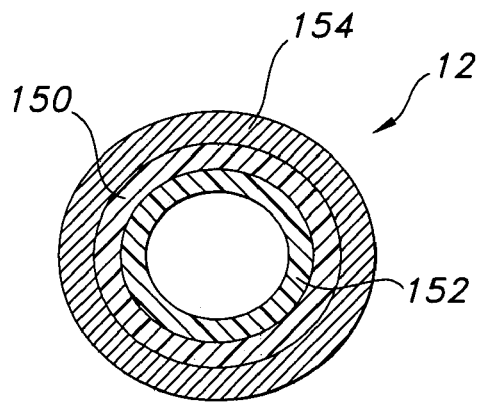
FIG. 31 is a cross-sectional view of the prosthesis of the present invention depicting a tubular wall having an exterior stent portion with a textile inner wall portion disposed on the inner surface of the stent and a polymeric inner layer portion disposed on the interior surface of the textile portion.
Figure 32:
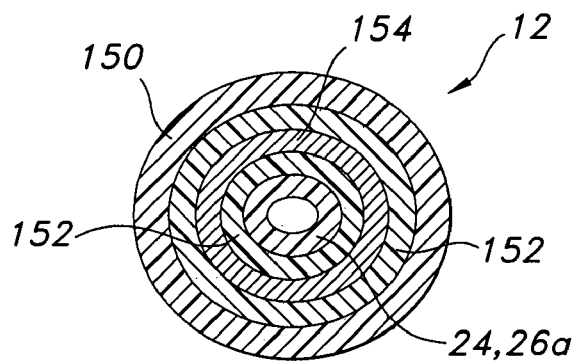
FIG. 32 is a cross-sectional view of the prosthesis of the present invention depicting a tubular wall having an exterior textile inner wall portion disposed over a first polymeric inner layer portion which is disposed on an outer surface of a stent with a second polymeric inner layer portion disposed on the inner surface of the stent and an interior textile portion disposed over the inner surface of the second polymeric layer.

The cross-sectional view of the textile prosthesis 10 is depicted in FIG. 9 as having a textile portion 150 as the cylindrical wall 12. The present invention, however, is not so limited, and the prosthesis may be a composite device as depicted in FIGS. 25-32. As depicted in FIG. 25, the cylindrical wall 12 may further include a polymeric layer or tube 152 circumferentially disposed about the textile portion 150. As depicted in FIG. 26, the polymeric layer or tube 152 may be circumferentially disposed about the exterior of the textile portion 150. Further, as depicted in FIG. 27, the cylindrical wall 12 may consist of the textile portion 150 and a stent 154 circumferentially disposed about the inner surface of the textile portion to define a stent-graft 156. The stent-graft 156 may optionally include the polymeric layer or tube 152 circumferentially disposed about the interior portions of stent 154, as depicted in FIG. 27, or circumferentially disposed about exterior portions of stent 154, as depicted in FIG. 28, or circumferentially disposed about both interior and exterior portions of stent 154, as depicted in FIG. 29. Alternatively, the polymeric layer or tube 152 may be directly associated with stent 154 to provide a unitary polymeric covered stent (not shown). Further, stent-graft 156 may be formed as having textile and/or polymeric portions disposed to interior portions of stent 154. As depicted in FIG. 30, stent-graft 156 may include stent 154 having the polymeric tube or layer 152 circumferentially disposed about the interior portions of the stent 154 with textile portion 150 being circumferentially disposed about the interior portions of the polymeric tube or layer 152. As depicted in FIG. 31, stent-graft 156 may alternatively include stent 154 having the textile portion 150 circumferentially disposed about the interior portions of the stent 154 with polymeric tube or layer 152 being circumferentially disposed about the interior portions of the textile portion 150. As depicted in FIG. 32, stent-graft 156 may alternatively include stent 154 having polymeric tubes or layers 152 circumferentially disposed over the interior and exterior stent surfaces with the textile portion 150 being circumferentially disposed about the polymeric tubes or layers 152 to provide a stent graft 156 having both interior and exterior textile surfaces. Further, although these composite devices have been described as being a cross-sectional view of the cylindrical wall 12 of prosthesis 10, such composite devices may suitably be or form portions of the tubular legs 16, 18 or of the tubular body 20 of bifurcated prosthesis 14.

Moreover, the prosthesis 10 may be crimped (not shown) along the tubular surface thereof to impart longitudinal compliance, kink resistance and enhanced handling characteristics. The crimp may be provided by placing a coil of metal or plastic wire (not shown) around a stainless steel mandrel. The prosthesis 10 is slid over the mandrel (not shown) and the coil wire. Another coil is wrapped around the assembly over the graft to fit between the spaces of the inner coil. The assembly is then heat set and results in the formation of the desired crimp pattern. It is further contemplated that other conventional crimping processes may also be used to impart a crimp to the prosthesis 10.

Moreover, prosthesis 10 may be formed as an implantable prosthesis which is self-supporting and usable to maintain patency of a bodily vessel, such as in the coronary vasculature, esophagus, trachea, colon, biliary tract, tracheal/bronchial tubes, urinary tract, prostate, and brain. Also, the textile portions or the yarns forming textile portions may be treated with any of the following therapeutic agents: anti-thrombogenic agents (such as heparin, heparin derivatives, urokinase, and PPack (dextrophenylalanine proline arginine chloromethylketone); anti-proliferative agents (such as enoxaprin, angiopeptin, or monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-miotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides); vascular cell growth promoters (such as growth factor inhibitors, growth factor receptor antagonists, transcriptional activators, and translational promotors); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous or vascoactive mechanisms.

The invention may be further understood with reference to the following non-limiting examples.

EXAMPLES

Example 1

Single Layer Stretch Knit Bifurcated Tubular Graft with a Two-Needle Underlap with Straight Tube (Body or Leg) Knitting Details The following specifications are used to fabricate a solid knitted prosthesis of the present invention.

Yarn Type: Texturized polyethylene terephthalate (PET), 40 denier, 27 filaments.

Machine Type: 60 Gauge Karl Mayer Machine (30 needles per inch).

Number of Guide Bars: Sixteen

Guide bars 1-8, if threaded, were used for knitting the front of the graft and guide bars 9-16, if threaded, were used for the rear of the graft.

| 16 Guide Bar Layout: | | | | | | | | | | | | | | | |
|---|---|---|---|---|---|---|---|---|---|---|---|---|---|---|---|
| 1 | 2 | 3 | 4 | 5 | 6 | 7 | 8 | 9 | 10 | 11 | 12 | 13 | 14 | 15 | 16 |
| G | G | 3-C-4 | | 5-C-6 | | 7-C-8 | | 9-C-10 | | 11-C-12 | | 13-C-14 | | G | G |

Notes:
G: Ground Bars
C: Nested Connect Bars

Guide Bar Threading Details: (Y—Threaded/n—Not Threaded)

72 Needle Bifurcated (BIF) Tube or Body

| Bar No. | Note: | ← | | | | (One Repeat Unit) | | | | | | → |
|---|---|---|---|---|---|---|---|---|---|---|---|---|
| #16 | not used | n | N | n | n | n | n | n | N | n | n | n |
| #15 |  | n | Y | Y | Y | Y | n | n | Y | Y | Y | n |
| #14 | R | Y | n | N | n | n | n | n | N | n | n | Y |
| #13 | CL |  | n | N | n | n | Y | n | N | n | n | n |
| #12 | R |  | n | N | n | n | n | n | N | n | n | Y | n |
| #11 | CR |  | n | N | n | n | n | Y | N | n | n | n |
| #10 | not used |  | n | N | n | n | n | n | N | n | n | n |
| #9 | not used |  | n | N | n | n | n | n | N | n | n | n |
| #8 | not used |  | n | N | n | n | n | n | N | n | n | n |
| #7 | not used |  | n | N | n | n | n | n | N | n | n | n |
| #6 | CR |  | n | N | n | n | n | Y | N | n | n | n |
| #5 | L |  | Y | n | N | n | n | n | n | N | n | n | n |
| #4 | CL | n | n | N | n | n | Y | n | N | n | n | n |
| #3 | L | Y | n | N | n | n | n | n | N | n | n | n |
| #2 |  | n | n | Y | Y | Y | Y | n | n | Y | Y | Y | Y |
| #1 | not used | n | n | N | n | n | n | n | N | n | n | n |

Notes:
L: left body connect
R: right body connect
CL: left leg connect
CR: right leg connect
Bars 4 and 6 join front bar 2
Bars 11 and 13 join back bar 15
Total needles for BIF is 72 * 2 or 144 needles 42 Needle Straight Tube (ST) or Leg

| Bar No. | Note: | ← | | | | (One Repeat Unit) | | | → |
|---|---|---|---|---|---|---|---|---|---|
| #16 | not used | n | n | n | n | n | n | n | n |
| #15 |  | n | Y | Y | Y | Y | Y | Y | n |
| #14 | R | Y | n | n | n | n | n | n | Y |
| #13 | CL |  | n | n | n | n | n | n | n |
| #12 | R |  | n | n | n | n | n | Y | n |
| #11 | CR |  | n | n | n | n | n | n | n |
| #10 | not used |  | n | n | n | n | n | n | n |
| #9 | not used |  | n | n | n | n | n | n | n |
| #8 | not used |  | n | n | n | n | n | n | n |
| #7 | not used |  | n | n | n | n | n | n | n |
| #6 | CR |  | n | n | n | n | n | n | n |
| #5 | L |  | Y | n | n | n | n | n | n |
| #4 | CL | n | n | n | n | n | n | n | n |
| #3 | L | Y | n | n | n | n | n | n | n |
| #2 |  | n | n | Y | Y | Y | Y | Y | n |
| #1 | not used | n | n | n | n | n | n | n | n |

Notes:
L: left body connect
R: right body connect
CL: left leg connect
CR: right leg connect
Bars 4 and 6 join front bar 2
Bars 11 and 13 join back bar 15
Total needles for ST is (40 for body + 2 for connector) * 2 for total of 84 needles Guide Bar Chain Notation Details Pattern Chains
Top Drum (Body): Channel 1

| Bar #1: | 0-0/0-0// | not used |
|---|---|---|
| Bar #2: | 0_2-0/4-4/4-6/2-2/ | 2-0/4-4/4-6/2-2_0// |
| Bar #3: | 0_4-2/4-4/2-2/2-0/ | 4-2/4-4/2-2/2-0// |
| Bar #4: | 0_2-0/4-4/4-6/2-2/ | 2-0/4-4/4-6/2-2_0// |
| Bar #5: | 0_2-0/2-2/4-4/4-2/ | 2-0/2-2/4-4/4-2_0// |
| Bar #6: | 0_2-0/4-4/4-6/2-2/ | 2-0/4-4/4-6/2-2_0// |
| Bar #7: | 0-0/0-0// |  |
| Bar #8: | 0-0/0-0// |  |
| Bar #9: | 0-0/0-0// |  |
| Bar #10: | 0-0/0-0// |  |
| Bar #11: | 0_2-2/4-6/2-2/2-0/ | 2-2/4-6/2-2/2-0// |
| Bar #12: | 0_2-2/2-4/0-2/0-0/ | 2-2/2-4/0-2/0-0// |
| Bar #13: | 0_2-2/4-6/2-2/2-0/ | 2-2/4-6/2-2/2-0// |
| Bar #14: | 0-0/0-2/2-4/2-2/ | 0-0/0-2/2-4/2-2_0// |
| Bar #15: | 0_2-2/4-6/2-2/2-0/ | 2-2/4-6/2-2/2-0// |
| Bar #16: | 0-0/0-0// | not used |

Pattern Chains
Bottom Drum (Legs): Channel 2

| Bar #1: | 0-0/0-0// | not used |
|---|---|---|
| Bar #2: | 0_2-0/4-4/4-6/2-2/ | 2-0/4-4/4-6/2-2_0// |
| Bar #3: | 0_4-2/4-4/2-2/2-0/ | 4-2/4-4/2-2/2-0// |
| Bar #4: | 0_2-2/4-4/6/2-2/ | 2-2/4-4/6/2-2_0// |
| Bar #5: | 0_2-0/2-2/4-4/4-2/ | 2-0/2-2/4-4/4-2_0// |
| Bar #6: | 0_2-0/2-2/4-4/4-2/ | 2-0/2-2/4-4/4-2_0// |
| Bar #7: | 0-0/0-0// |  |
| Bar #8: | 0-0/0-0// |  |
| Bar #9: | 0-0/0-0// |  |
| Bar #10: | 0-0/0-0// |  |
| Bar #11: | 0_4-2/4-4/2-2/2-0/ | 4-2/4-4/2-2/2-0// |
| Bar #12: | 0_2-2/2-4/0-2/0-0/ | 2-2/2-4/0-2/0-0// |
| Bar #13: | 0_2-2/4-6/2-4/2-2/ | 2-2/4-6/2-4/2-2_0// |
| Bar #14: | 0-0/0-2/2-4/2-2/ | 0-0/0-2/2-4/2-2_0// |
| Bar #15: | 0_2-2/4-6/2-2/2-0/ | 2-2/4-6/2-2/2-0// |
| Bar #16: | 0-0/0-0// | not used |

Graft Processing:

Subsequent to knitting the textile graft, the material is scoured in a basic solution of warm water (e.g., about 65° C.

or about 150° F.) and cleaning detergent. It is then rinsed to remove the cleaning agents. The graft is then compacted with methylene chloride at elevated temperatures, for instance about 107° C. or about 224° F., for a short period of time, for instance, three minutes.

Example 2

Single Layer Knit Tubular Graft with a Three Needle Underlap

The following specifications are used to fabricate a solid knitted prosthesis of the present invention.

Yarn Type: Texturized polyethylene terephthalate (PET), 40 denier, 27 filaments.

Machine Type: 56 Gauge Kiddie Machine (28 needles per inch).

Number of Guide Bars: Eight

| Guide Bar Threading Details: (y - Threaded/n - Not Threaded) |
|---|
| Guide Bar No. 8: y/y/y/y/y/y/y/y/n/n |
| Guide Bar No. 7: y/n/n/n/n/n/n/n/n/n |
| Guide Bar No. 6: n/n/n/n/n/n/n/n/n/y |
| Guide Bar No. 5: y/n/n/n/n/n/n/n/n/n |
| Guide Bar No. 4: n/n/n/n/n/n/n/n/y/n |
| Guide Bar No. 3: y/n/n/n/n/n/n/n/n/n |
| Guide Bar No. 2: y/n/n/n/n/n/n/n/n/n |
| Guide Bar No. 1: y/y/y/y/y/y/y/y/n/n |

| Guide Bar Position Details: |
|---|
| Guide Bar No. 1: 6-8-4-4/2-0-4-4/(repeat) Front Full Thread |
| Guide Bar No. 8: 4-4-2-0/4-4-6-8/(repeat) Back Full Thread |
| Guide Bar No. 2: 4-6-2-2/0-0-0-2/(repeat) Right Connect |
| Guide Bar No. 4: 2-4-0-0/2-2-2-4/(repeat) Right Connect |
| Guide Bar No. 6: 0-2-2-2/4-4-4-6/(repeat) Right Connect |
| Guide Bar No. 3: 2-2-2-0/6-4-4-4/(repeat) Left Connect |
| Guide Bar No. 5: 4-4-4-2/4-2-6-6/(repeat) Left Connect |
| Guide Bar No. 7: 6-6-6-4/2-0-4-4/(repeat) Left Connect |

Graft Processing:

Subsequent to knitting the textile graft, the material is scoured in a basic solution of warm water (e.g., about 65° C. or about 150° F.) and cleaning detergent. It is then rinsed to remove the cleaning agents. The graft is then compacted with methylene chloride at elevated temperatures, for instance about 107° C. or about 224° F., for a short period of time, for instance, three minutes.

Example 3

Single Layer Stretch Knit Straight Tubular Graft with a Two-Needle Underlap

The following specifications were used to fabricate a super stretch knitted prosthesis of the present invention.

Yarn Type Used: Texturized polyethylene terephthalate (PET), 40 denier, 27 filaments.

Machine Used: 56 Gauge Kiddie Machine (28 needles per inch)

Guide Bars Used: 6

| Guide Bar Threading Details: (y - threaded, n - not threaded): | | | | | | | | | | | |
|---|---|---|---|---|---|---|---|---|---|---|---|
| Guide Bar No. 6 | n | n | y | y | y | Y | y | y | y | y | n |
| Guide Bar No. 5 | n | y | n | n | n | N | n | n | n | n | n |
| Guide Bar No. 4 | n | n | n | n | n | N | n | n | n | n | y |
| Guide Bar No. 3 | n | n | n | n | n | N | n | n | n | y | n |
| Guide Bar No. 2 | y | n | n | n | n | N | n | n | n | n | n |
| Guide Bar No. 1 | n | n | y | y | y | Y | y | y | y | y | n |

| Guide Bar Chain Notation Details: | | |
|---|---|---|
| Guide Bar No. 1: | 2-0/4-4/4-6/2-2// repeat | Front full thread |
| Guide Bar No. 2: | 4-2/4-4/2-2/2-0// repeat | Left connector |
| Guide Bar No. 3: | 2-2/2-4/0-2/0-0// repeat | Right connector |
| Guide Bar No. 4: | 0-0/0-2/2-4/2-2// repeat | Right connector |
| Guide Bar No. 5: | 2-0/2-2/4-4/4-2// repeat | Left connector |
| Guide Bar No. 6: | 2-2/4-6/2-2/2-0// repeat | Back full thread |

Graft Processing:

Subsequent to knitting the textile graft, the material was scoured in a basic solution of warm water (e.g., about 65° C. or about 150° F.) and cleaning detergent. It was then rinsed to remove the cleaning agents. The graft was then compacted with methylene chloride at elevated temperatures, for instance about 107° C. or about 224° F., for a short period of time, for instance, three minutes.

Example 4

Single Layer Stretch Knit Bifurcated Tubular Graft with a Two-Needle Underlap

The following specifications were used to fabricate a bifurcated super stretch knitted prosthesis of the present invention.

Yarn Type Used: Texturized polyethylene terephthalate (PET), 40 denier, 27 filaments.

Machine Used: 56 Gauge Kiddie Machine (28 needles per inch)

Guide Bars Used: 10

| Guide Bar Threading Details: (y - threaded, n - not threaded): | | | | | | | | | | | |
|---|---|---|---|---|---|---|---|---|---|---|---|
| Guide Bar No. 10 | n | n | y | y | y | y | n | n | y | y | y | n |
| Guide Bar No. 9 | n | y | n | n | n | n | n | n | n | n | n | n |
| Guide Bar No. 8 | n | n | n | n | n | n | n | n | n | n | n | y |
| Guide Bar No. 7 | n | n | n | n | n | y | n | n | n | n | n | n |
| Guide Bar No. 6 | n | n | n | n | n | n | n | y | n | n | n | n |
| Guide Bar No. 5 | n | n | n | n | n | n | y | n | n | n | n | n |
| Guide Bar No. 4 | n | n | n | n | n | n | y | n | n | n | n | n |
| Guide Bar No. 3 | n | n | n | n | n | n | n | n | n | n | y | n |

-continued

Guide Bar Threading Details: (y - threaded, n - not threaded):

| Guide Bar No. 2 | y | n | n | n | n | n | n | n | n | n | n |
|---|---|---|---|---|---|---|---|---|---|---|---|
| Guide Bar No. 1 | n | n | y | y | y | y | n | n | y | y | y | n |

Guide Bar Chain Notation Details:

| Guide Bar No. 1: | 2-0/4-4/4-6/2-2// repeat | Front full thread |
|---|---|---|
| Guide Bar No. 2: | 4-2/4-4/2-2/2-0// repeat | Left connector |
| Guide Bar No. 3: | 2-2/2-4/0-2/0-0// repeat | Right connector |
| Guide Bar No. 4 Leg: | 4-4/4-2/2-0/2-2// repeat | Bifurcation connector |
| Guide Bar No. 4 Body: | 4-6/2-2/2-0/4-4// repeat | Join Bar No. 1 |
| Guide Bar No. 5 Leg: | 4-6/4-4/2-2/2-4// repeat | Bifurcation connector |
| Guide Bar No. 5 Body: | 4-6/2-2/2-0/4-4// repeat | Join Bar No. 1 |
| Guide Bar No. 6 Leg: | 2-4/2-2/2-4/4-6// repeat | Bifurcation connector |
| Guide Bar No. 6 Body: | 2-2/2-0/4-4/4-6// repeat | Join Bar No. 10 |
| Guide Bar No. 7 Leg: | 2-2/2-0/4-2/4-4// repeat | Bifurcation connector |
| Guide Bar No. 7 Body: | 2-2/2-0/4-4/4-6// repeat | Join Bar No. 10 |
| Guide Bar No. 8: | 0-0/0-2/2-4/2-2// repeat | Right connector |
| Guide Bar No. 9: | 2-0/2-2/4-4/4-2// repeat | Left connector |
| Guide Bar No. 10: | 2-2/4-6/2-2/2-0// repeat | Back full thread |

Graft Processing:

Subsequent to knitting the textile graft, the material was scoured in a basic solution of warm water (e.g., about 65° C. or about 150° F.) and cleaning detergent. It was then rinsed to remove the cleaning agents. The graft was then compacted with methylene chloride at elevated temperatures, for instance about 107° C. or about 224° F., for a short period of time, for instance, three minutes.

Example 5

Reorientation of a Single Layer Stretch Knit Tubular Graft with a Two-Needle Underlap High stretch, flat knitted straight tubular (ST) graft were warp knitted with a two needle underlap and a one needle overlap in accordance with the present invention. Two different sized tubes were knitted. Details of the grafts prior reorientation of the radially extending yarns are shown below in Table 6.

TABLE 6

ST Graft Properties Prior to Radial Expansion

|  | Knit Size | |
|---|---|---|
| Description: | 42 Tube | 45 Tube |
| Needles Used per Side | 42 | 45 |
| Stitch Density |  |  |
| Courses per inch | 140 | 140 |
| Graft Flat Width, mm | 10 | 11.5 |
| Corresponding Tubular Diameter, mm[1] | 6.4 | 7.3 |

Notes:
[1] Estimated from graft flat width.

The straight knit grafts were then radially expanded by sliding the grafts over a stainless steel mandrel having a rounded end. The grafts were easily slid over the mandrel by simple manual manipulation. Sliding the grafts over the mandrel reoriented the yarns. The grafts were heat set to fix the yarns in the reoriented pattern and to set the graft in a substantially tubular shape. Details are shown below in table 7.

TABLE 7

ST Graft Properties After Radial Expansion

|  | Knit Size | |
|---|---|---|
| Description | 42 Tube | 45 Tube |
| Mandrel diameter, mm | 15.3 | 17.3 |
| Graft flat width after heat setting, mm | 24.0 | 27.2 |
| Corresponding tubular diameter, mm | 15.3 | 17.3 |
| Heat Setting temperature, ° C. | 200 | 200 |
| Heat Setting Time, minutes | 10 | 10 |
| Stitch Density |  |  |
| Courses per inch | 140 | 140 |

Notes:
(1) Estimated from graft flat width.

Example 6

Reorientation of a Bifurcated (BIF) Single Layer Stretch Knit Tubular Graft with a Two-Needle Underlap High stretch, flat knitted bifurcated tubular (BIF) graft were warp knitted with a two needle underlap and a one needle overlap in accordance with the present invention. Two different sized tubes were knitted. Details of the grafts prior reorientation of the radially extending yarns are shown below in Table 8.

TABLE 8

BIF Graft Properties Prior to Radial Expansion

|  | Knit Size | |
|---|---|---|
| Description: | 72 BIF | 78 BIF |
| Needles Used per Side | 72 | 78 |
| Graft Flat Width, mm |  |  |
| main body, mm | 18 | 19 |
| legs, mm | 9 | 10 |
| Corresponding Tubular Diameter, mm[1] | 6.4 | 7.3 |
| main body, mm | 11.5 | 12.1 |
| legs, mm | 5.7 | 6.4 |

Notes:
[1] Estimated from graft flat width.

The bifurcated knitted grafts were then radially expanded by sliding the grafts over a stainless steel bifurcated mandrel having two rounded ends. The grafts were easily slid over the mandrel by simple manual manipulation. Sliding the grafts over the mandrel reoriented the yarns. The grafts were heat set to fix the yarns in the reoriented pattern and to set the graft in a substantially tubular shape. Details are shown below in table 9.

TABLE 9

BIF Graft Properties After Radial Expansion

| | Knit Size | |
|---|---|---|
| Description: | 42 Tube | 45 Tube |
| Mandrel diameter, mm | | |
| main body, mm | 28.3 | 30.3 |
| legs, mm | 14.2 | 15.2 |
| Graft flat width after heat setting, mm | | |
| main body, mm | 44.5 | 47.6 |
| legs, mm | 22.3 | 23.8 |
| Corresponding tubular diameter, mm | | |
| main body, mm | 28.3 | 30.3 |
| legs, mm | 14.2 | 15.2 |
| Heat Setting temperature, ° C. | 200 | 200 |
| Heat Setting Time, minutes | 10 | 10 |
| Stitch Density (main body and legs) | | |
| Courses per inch | 140 | 140 |

Notes:
(1) Estimated from graft flat width.

Example 7

Dilation Testing Results—Force Applied to the Coarse Direction of the Graft

A 1 inch sample was cut from the radially expanded and heat set graft of Example 6. A 1 inch sample of a conventional double-velour knitted graft, commercially available as Hemashield® from Boston Scientific Corporation, Wayne, N.J., was also cut. The cut samples were then placed under different force loads along the course direction, which corresponds to radially expanding the corresponding tubular structure. Details are provided below in Table 10.

TABLE 10

Dilation Testing

| | Radially Expanded, Heat Set, High Stretch Graft Sample | Heat Set, Graft Sample (Control) |
|---|---|---|
| Percent Stretch or Elongation at a one pound-force (1 lb$_f$) Applied to the Course Direction | 5.6% | 26.3% |
| Percent Stretch or Elongation at a two pound-force (2 lb$_f$) Applied to the Course Direction | 9.6% | 38.3% |
| Thickness of graft sample, mm | 0.3 | ~2 |

The radially expanded, high stretch knit grafts having a reoriented and heat set yarn pattern had improved resistance to dilation, as noted by the lower amounts of stretching as compared to the control. The improved resistance to dilation is evident despite a significantly smaller wall thickness of the graft of the present invention as compared to the commercially available sample. For example, it has been reported that knitted grafts in repair of abdominal aortic aneurysms in human patients had a mean graft dilation (or increase in graft diameter) or 42.6 percent and woven grafts had a mean graft dilation of 25.5 percent. See, D. A. Robinson et al., Graft Dilation Following Abdominal Aortic Aneurysm Resection and Grafting, Aust. N.Z. J. Surg. (1999) 69, 849-851. Further, in another study Hemashield® knitted grafts were reported to have a graft aorta dilation of about 21.5 percent. See, A. Ippoliti et al., Dacron Knitted Graft Dilation Assessment With Helical CT Scanning After Aortoiliac Surgery, G. Ital. Chir. Vasc. 2000, 7/3 (201-213) (Italian). Thus, the knitted grafts of the present invention have improved resistance against dilation over both convention knitted and woven grafts.

Example 8

Dilation Testing Results—Pressurized Water Loop Flow

A bifurcated graft with a one needle overlap and a two needle underlap having a nominal 26 mm diameter main tubular body and nominal 13 mm bifurcated tubular legs was knitted according to the details of Example 4 and radially stretched and heat-set according to the details of Example 5. The graft was placed under internal pressure of 2.3 psi (or about 120 mm Hg) with pressurized water, which was pressurized through a flow loop including the graft with a pump. The diameter of the main tubular body was measured at six different points along the length of the main tubular body over time to determine the graft dilation. The measurement at day zero represents the initial graft diameter before dilation testing. Details are shown below in Table 11.

TABLE 11

Dilation Testing - Pressurized Water Flow Loop at 2.3 psi

| | Sample Point | | | | | | | Std. | % Dilation |
|---|---|---|---|---|---|---|---|---|---|
| Days | 1 | 2 | 3 | 4 | 5 | 6 | Average | Dev. | |
| 0 | 25.6 | 25.2 | 25.5 | 25.3 | 25.3 | 25.5 | 25.4 | 0.2 | |
| 1 | 26.6 | 26.2 | 26.3 | 25.7 | 26.7 | 26.0 | 26.2 | 0.4 | 3.3 |
| 2 | 26.9 | 26.3 | 26.6 | 26.0 | 26.8 | 25.3 | 26.3 | 0.6 | 3.7 |
| 3 | 26.5 | 26.3 | 26.7 | 26.1 | 26.7 | 26.4 | 26.5 | 0.2 | 4.2 |
| 4 | 26.5 | 26.0 | 26.5 | 26.2 | 26.7 | 26.4 | 26.4 | 0.3 | 3.9 |
| 7 | 27.0 | 26.1 | 26.9 | 26.4 | 26.9 | 26.7 | 26.7 | 0.3 | 5.0 |
| 8 | 26.9 | 26.1 | 26.7 | 26.2 | 26.9 | 27.0 | 26.6 | 0.4 | 4.9 |
| 9 | 27.1 | 26.7 | 27.0 | 26.3 | 27.0 | 27.0 | 26.8 | 0.3 | 5.7 |
| 10 | 27.1 | 26.7 | 27.2 | 26.5 | 27.0 | 27.0 | 26.9 | 0.2 | 6.0 |
| 11 | 27.1 | 26.9 | 27.1 | 26.6 | 27.1 | 27.1 | 27.0 | 0.2 | 6.3 |
| 14 | 27.1 | 27.0 | 27.1 | 26.7 | 27.1 | 27.0 | 27.0 | 0.2 | 6.3 |
| 21 | 27.2 | 27.0 | 27.1 | 26.8 | 27.1 | 27.0 | 27.0 | 0.1 | 6.5 |
| 28 | 27.1 | 26.9 | 27.1 | 26.8 | 27.1 | 27.0 | 27.0 | 0.1 | 6.3 |
| 35 | 27.1 | 26.9 | 27.1 | 26.8 | 27.1 | 27.1 | 27.0 | 0.1 | 6.4 |
| 42 | 27.1 | 26.9 | 27.1 | 26.8 | 27.1 | 27.1 | 27.0 | 0.1 | 6.4 |
| 49 | 27.1 | 26.9 | 27.0 | 26.8 | 27.1 | 27.1 | 27.0 | 0.1 | 6.4 |
| 56 | 27.1 | 27.0 | 27.0 | 26.8 | 27.1 | 27.1 | 27.0 | 0.1 | 6.4 |
| 63 | 27.1 | 26.9 | 27.0 | 26.8 | 27.1 | 27.1 | 27.0 | 0.1 | 6.4 |

The test results show that the knitted grafts of the present invention exhibit improved dilation resistance over time. The maximum dilation was about 6.4 percent over 63 days. Further, the dilation stabilized at about day 11, after which dilation remained substantially constant.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A method for providing dilation resistance to an implantable tubular graft comprising:

(a) providing a graft comprising opposed open ends and a textile wall extending in a lengthwise direction therebetween defining a graft diameter, wherein the textile wall comprises radially extending yarns having a radial extent which inter-engage longitudinally extending yarns having a longitudinal extent to define a textile pattern and further wherein the radially extending yarns are obliquely oriented to the lengthwise direction of the graft, thereby defining a first acute angle from the lengthwise direction of the graft;

(b) providing an elongate tubular mandrel having a diameter which differs from the graft diameter by a factor of at least 1.5;

(c) positioning the graft over the mandrel to radially distend the graft, thereby reorienting the radially extending yarns to reduce the radial extent and to shift the radially extending yarns to a second acute angle from the lengthwise direction of the graft to define an reoriented textile pattern, wherein the second acute angle is greater than the first acute angle; and (d) heat setting the graft at a first temperature to set the inter-engaging yarns in the reoriented textile pattern to provide a graft with improved dilation resistance.

2. The method of claim 1, wherein the mandrel has a diameter from about 1.5 to about 3.0 times greater than the diameter of the graft.

3. The method of claim 1, wherein said mandrel comprises of a non-elastomeric material.

4. The method of claim 1, wherein said mandrel comprises of a metallic material.

5. The method of claim 1, wherein said mandrel comprises of a stainless steel material.

6. The method of claim 1, wherein said radially extending yarns and said longitudinally extending yarns are inelastic yarns.

7. The method of claim 1, wherein said radially extending yarns and said longitudinally extending yarns are fully drawn, non-texturized polyethylene terephthalate yarns.

8. The method of claim 1, wherein the textile pattern is a knitted textile pattern.

9. The method of claim 8, wherein the knitted textile pattern is a high stretch knit pattern having a one needle overlap and a two needle or greater underlap.

10. The method of claim 1, wherein the step of positioning the graft over the mandrel further includes radially distending the graft without a substantially changing the length of the graft.

11. The method of claim 1, wherein said textile pattern is a braided pattern.

12. The method of claim 1, wherein the step of providing a mandrel includes providing at least two mandrels of different diameters, and wherein the step of positioning the graft includes positioning the graft over a first mandrel and then positioning the graft over the second mandrel, wherein the diameter of the second mandrel is larger than the diameter of the first mandrel.

13. The method of claim 1, wherein the mandrel has a rounded end and the graft is passed over the rounded end of the mandrel.

14. The mandrel of claim 1, wherein the mandrel is tapered to provide a first end with a first diameter and a second end with a second diameter, wherein the second diameter is larger that the first diameter and further wherein the second diameter is at least a multiplicative factor of 1.5 times greater than the graft diameter.

15. The method of claim 14, the step of positioning the graft further includes positioning the graft over the first end of the mandrel and sliding the graft towards the second end of the mandrel.

16. The method of claim 15, wherein the first end of the mandrel is a rounded end.

17. The method of claim 1, wherein the mandrel has a smooth exterior surface with a roughness less than about 0.2 micrometers.

18. The method of claim 1, wherein the graft is a bifurcated graft.

19. The method of claim 18, wherein the mandrel is a bifurcated mandrel.

20. The method of claim 1, further including the step of:
removing the graft from the mandrel after the heat-setting of the graft;
positioning the graft over a second mandrel which has a smaller diameter than the elongate tubular mandrel; and
heat setting the graft over the second mandrel at a second heat-setting temperature which is greater than the first heat-setting temperature.

21. The method of claim 20, further including the step of positioning a tubular layer or sheet of expanded polytetrafluoroethylene over the second mandrel prior to the step of positioning the graft on the second mandrel.

22. The method of claim 21, wherein the second heat-setting temperature bond portions of the expanded polytetrafluoroethylene to portions of the graft.

23. The method of claim 21, wherein the graft is a bifurcated graft having a main tubular graft body and at least two tubular graft legs extending from one end of the main tubular graft body; the mandrel is a bifurcated mandrel having a main tubular mandrel body portion and at least two tubular mandrel leg portions extending from one end of the main tubular mandrel body; and the expanded polytetrafluoroethylene is positioned over at least one of the mandrel portions.

24. A graft made by the method of claim 1, wherein the graft has less than about 15 percent radial elongation under a force of about two pounds-force.

25. The graft of claim 24 further comprising a stent circumferentially disposed about an interior portion of the textile wall or an exterior portion of the textile wall.

26. The graft of claim 24 further comprising a tubular layer or sheet of expanded polytetrafluoroethylene circumferentially disposed about an interior portion of the textile wall or an exterior portion of the textile wall.

27. The graft of claim 26 further comprising a stent circumferentially disposed about an interior portion or an exterior portion of the textile wall or about an interior portion or an exterior portion of the expanded polytetrafluoroethylene.

28. A graft made by the method of claim 1, wherein the graft is a knitted graft having a one needle overlap and a two needle or greater underlap and having a wall thickness of less than about 0.4 mm.

29. A graft made by the method of claim 28, wherein the graft has less than about 15 percent radial elongation under a force of about two pounds-force.

30. The graft of claim 29 further comprising a stent circumferentially disposed about an interior portion or an exterior portion of the textile wall or about an interior portion or an exterior portion of the expanded polytetrafluoroethylene.

31. A graft made by the method of claim 21, wherein the graft does not expand in diameter when subjected to normal physiological pressures within body lumens.

32. A method for providing dilation resistance to an implantable tubular graft comprising:
   (a) providing a graft comprising opposed open ends and a textile wall extending in a lengthwise direction therebetween defining a graft diameter, wherein the textile wall comprises course yarns having a radial extent which inter-loop wale yarns having a longitudinal extent to define a knitted textile pattern and further wherein the course yarns are obliquely oriented to the lengthwise direction of the graft, thereby defining a first acute angle from the lengthwise direction of the graft;
   (b) providing an elongate tubular mandrel having a diameter which is greater than the graft diameter by a factor of at least 1.5;
   (c) positioning the graft over the mandrel to radially distend the graft, thereby reorienting the course yarns to reduce the radial extent and to shift the course yarns to a second acute angle from the lengthwise direction of the graft to define a reoriented textile pattern, wherein the second acute angle is greater than the first acute angle; and
   (d) heat setting the graft at a first temperature to set the inter-looping yarns in the reoriented textile pattern to provide a graft with improved dilation resistance.

33. The method of claim 32, wherein the knitted pattern is a warp knitted pattern.

34. The method of claim 32, wherein the mandrel has a diameter from about 1.5 to about 3.0 times greater than the diameter of the graft.

35. The method of claim 32, wherein said mandrel comprises of a non-elastomeric material.

36. The method of claim 32, wherein said mandrel comprises of a metallic material.

37. The method of claim 32, wherein said mandrel comprises of a stainless steel material.

38. The method of claim 32, wherein said course yarns and said wale yarns are inelastic yarns.

39. The method of claim 32, wherein said course yarns and said wale yarns are fully drawn, non-texturized polyethylene terephthalate yarns.

40. The method of claim 32, wherein the knitted textile pattern is a high stretch knit pattern having a one needle overlap and a two needle or greater underlap.

41. The method of claim 32, wherein the step of positioning the graft over the mandrel further includes radially distending the graft without a substantially changing the length of the graft.

42. The method of claim 32, wherein the step of providing a mandrel includes providing at least two mandrels of different diameters, and wherein the step of positioning the graft includes positioning the graft over a first mandrel and then positioning the graft over the second mandrel, wherein the diameter of the second mandrel is larger than the diameter of the first mandrel.

43. The method of claim 32, wherein the mandrel has a rounded end and the graft is passed over the rounded end of the mandrel.

44. The mandrel of claim 32, wherein the mandrel is tapered to provide a first end with a first diameter and a second end with a second diameter, wherein the second diameter is larger that the first diameter and further wherein the second diameter is at least a multiplicative factor of 1.5 times greater than the graft diameter.

45. The method of claim 44, the step of positioning the graft further includes positioning the graft over the first end of the mandrel and sliding the graft towards the second end of the mandrel.

46. The method of claim 45, wherein the first end of the mandrel is a rounded end.

47. The method of claim 32, wherein the mandrel has a smooth exterior surface with a roughness less than about 0.2 micrometers.

48. The method of claim 32, wherein the graft is a bifurcated graft.

49. The method of claim 48, wherein the mandrel is a bifurcated mandrel.

50. The method of claim 32, further including the step of:
   removing the graft from the mandrel after the heat-setting of the graft;
   positioning a tubular layer or sheet of expanded polytetrafluoroethylene over a second mandrel which has a smaller diameter than the elongate tubular mandrel;
   positioning the graft over the second mandrel; and
   heat setting the tubular layer or sheet of expanded polytetrafluoroethylene and the graft over the second mandrel at a second heat-setting temperature which is greater than the first heat-setting temperature.

51. The method of claim 50, wherein the second heat-setting temperature bond portions of the expanded polytetrafluoroethylene to portions of the graft.

52. The method of claim 50, wherein the graft is a bifurcated graft having a main tubular graft body and at least two tubular graft legs extending from one end of the main tubular graft body; the mandrel is a bifurcated mandrel having a main tubular mandrel body portion and at least two tubular mandrel leg portions extending from one end of the main tubular mandrel body; and the expanded polytetrafluoroethylene is positioned over at least one of the mandrel portions.

53. A graft made by the method of claim 50, wherein the graft has less than about 15 percent radial elongation under a force of about two pounds-force.

54. The graft of claim 53 further comprising a stent circumferentially disposed about an interior portion or an exterior portion of the textile wall or about an interior portion or an exterior portion of the expanded polytetrafluoroethylene.

55. A graft made by the method of claim 50, wherein the graft is a knitted graft having a one needle overlap and a two needle or greater underlap and having a wall thickness of less than about 0.4 mm.

56. A graft made by the method of claim 32, wherein the graft has less than about 15 percent radial elongation under a force of about two pounds-force.

57. The graft of claim 56 further comprising a stent circumferentially disposed about an interior portion of the textile wall or an exterior portion of the textile wall.

58. The graft of claim 56 further comprising a tubular layer or sheet of expanded polytetrafluoroethylene circumferentially disposed about an interior portion of the textile wall or an exterior portion of the textile wall.

59. The graft of claim 58 further comprising a stent circumferentially disposed about an interior portion or an exterior portion of the textile wall or about an interior portion or an exterior portion of the expanded polytetrafluoroethylene.

60. A graft made by the method of claim 32, wherein the graft is a knitted graft having a one needle overlap and a two needle or greater underlap and having a wall thickness of less than about 0.4 mm.

61. A medical device comprising:
   a graft comprising opposed open ends and a textile wall extending in a lengthwise direction therebetween defining a graft diameter; wherein the textile wall comprises radially extending yarns selectively inter-knitted with longitudinally extending yarns to define a knitted textile pattern with a one needle overlap and a two needle or greater underlap, wherein the graft has a wall thickness of less than about one millimeter and wherein the radially extended yarns are reoriented to a radial orientation to improve resistence against dilation whereby the graft expands less than 15 percent in diameter when subjected to normal physiological pressures within body lumens.

62. The graft of claim 61 further comprising a stent circumferentially disposed about an interior portion of the textile wall or an exterior portion of the textile wall.

63. The graft of claim 61 further comprising a tubular layer or sheet of expanded polytetrafluoroethylene circumferentially disposed about an interior portion of the textile wall or an exterior portion of the textile wall.

64. The graft of claim 63 further comprising a stent circumferentially disposed about the interior portion or the exterior portion of the textile wall or about an interior portion or an exterior portion of the expanded polytetrafluoroethylene.

65. The graft of claim 61, wherein the graft expands less than 10 percent in diameter when subjected to an internal pressure of about 120 mm Hg.

66. The graft of claim 61, wherein the graft expands less than 7 percent in diameter when subjected to an internal pressure of about 120 mm Hg.

67. The device of claim 61, wherein the wall thickness of the graft is less than about 0.4 millimeters.

* * * * *

UNITED STATES PATENT AND TRADEMARK OFFICE
CERTIFICATE OF CORRECTION

| | | |
|---|---|---|
| PATENT NO. | : 7,364,587 B2 | |
| APPLICATION NO. | : 10/938919 | |
| DATED | : April 29, 2008 | |
| INVENTOR(S) | : Dong et al. | |

It is certified that error appears in the above-identified patent and that said Letters Patent is hereby corrected as shown below:

At column 2, line 39, the printed patent should read --...radially expanding yarns...--.

At column 3, line 26, the printed patent should read --...is larger than the first...--.

At column 8, line 7, the printed patent should read "...prosthesis 10 is knitted as a substantially...--.

At column 9, line 14, the printed patent should read --...interlooping with yarn 32d.--.

At column 17, line 41, the printed patent should read --...graft diameter as knitted or braided.--.

At column 19, line 31, the printed patent should read --...used in conjunction with the devices...--.

At column 29, line 64, the printed patent should read --...increase in graft diameter) of 42.6 percent...--.

At column 31, line 47, claim 10, the printed patent should read --...graft without substantially changing...--.

At column 33, line 46, claim 41, the printed patent should read --...graft without substantially changing...--.

UNITED STATES PATENT AND TRADEMARK OFFICE
CERTIFICATE OF CORRECTION

PATENT NO.        : 7,364,587 B2
APPLICATION NO.   : 10/938919
DATED             : April 29, 2008
INVENTOR(S)       : Dong et al.

It is certified that error appears in the above-identified patent and that said Letters Patent is hereby corrected as shown below:

At column 33, line 61, claim 44, the printed patent should read --...is larger than the first diameter...--.

Signed and Sealed this

Nineteenth Day of August, 2008

JON W. DUDAS
*Director of the United States Patent and Trademark Office*